(12) United States Patent
Siekmeier

(10) Patent No.: US 10,720,242 B2
(45) Date of Patent: Jul. 21, 2020

(54) SYSTEMS AND METHODS FOR MODELING AND PREDICTING EFFECTIVE TREATMENTS FOR SCHIZOPHRENIA AND OTHER DISORDERS

(71) Applicant: Peter J. Siekmeier, Cambridge, MA (US)

(72) Inventor: Peter J. Siekmeier, Cambridge, MA (US)

(73) Assignee: MCLEAN HOSPITAL CORPORATION, Belmont, MA (US)

( * ) Notice: Subject to any disclaimer, the term of this patent is extended or adjusted under 35 U.S.C. 154(b) by 1114 days.

(21) Appl. No.: 14/961,729

(22) Filed: Dec. 7, 2015

(65) Prior Publication Data

US 2016/0162652 A1 Jun. 9, 2016

Related U.S. Application Data

(60) Provisional application No. 62/088,024, filed on Dec. 5, 2014.

(51) Int. Cl.
*G16H 50/50* (2018.01)
*A61B 5/00* (2006.01)
*A61B 5/0484* (2006.01)
*G16H 50/20* (2018.01)
*A61B 5/04* (2006.01)

(52) U.S. Cl.
CPC ......... *G16H 50/50* (2018.01); *A61B 5/04845* (2013.01); *A61B 5/4848* (2013.01); *G16H 50/20* (2018.01); *A61B 5/04009* (2013.01); *A61B 5/4088* (2013.01)

(58) Field of Classification Search
None
See application file for complete search history.

(56) References Cited

U.S. PATENT DOCUMENTS

| | | | | |
|---|---|---|---|---|
| 7,945,392 B2 * | 5/2011 | Siekmeier | ................ | G06N 3/02 702/19 |
| 8,150,629 B2 * | 4/2012 | Geerts | .................... | G16H 50/50 702/19 |
| 8,588,899 B2 * | 11/2013 | Schiff | .................. | A61B 5/0478 600/544 |
| 2006/0089824 A1 * | 4/2006 | Siekmeier | ............. | G06F 19/704 703/11 |
| 2007/0106479 A1 * | 5/2007 | Geerts | .................... | G16H 50/50 702/19 |

(Continued)

OTHER PUBLICATIONS

Siekmeier, Peter J.; Evidence of multistability in a realistic computer simulation of hippocampus subfield CA1.; Elsevier; Behavioural Brain Research 200 (2009) 220-231. (Year: 2009).*

(Continued)

*Primary Examiner* — Stanley K. Hill
(74) *Attorney, Agent, or Firm* — Quarles & Brady LLP

(57) ABSTRACT

A system and method for evaluating an effectiveness of a therapy for a psychological condition includes selecting a therapy to be analyzed relative to psychological pathology. The selected therapy is applied to a model of the psychological condition that includes hyperdopaminergia as a function. A response is determined using an output of the model of the psychological condition. The response is compared to a control to determine a wellness metric and a report is generated indicating an effectiveness of the therapy based on the wellness metric.

30 Claims, 6 Drawing Sheets
(1 of 6 Drawing Sheet(s) Filed in Color)

(56) References Cited

U.S. PATENT DOCUMENTS

2008/0027651 A1* 1/2008 Siekmeier ............... G06N 3/02
702/19
2013/0331394 A1* 12/2013 Siekmeier .......... G01N 33/5088
514/249

OTHER PUBLICATIONS

VanMaanen, David P. et al; Development of Antipsychotic Medications with Novel Mechanisms of Action Based on Computational Modeling of Hippocampal Neuropathology; Plus One; Mar. 2013, vol. 8, Issue 3, pp. 1-13. (Year: 2013).*

VanMaanen, David P. et al; Dopaminergic Contributions to Hippocampal Pathophysiology in Schizophrenia: A Computational Study; Neuropsychopharmacology (2014) 39, 1713-1721. (Year: 2014).*

Rolls, Edmund T. et al.; Computational models of schizophrenia and dopamine modulation in the prefrontal cortex; 2008; Macmilan Pulishers Limited; Nature Reviews|Neuroscience, vol. 9; pp. 695-709. (Year: 2008).*

Rolls, Edmund T. et al.; A computational neuroscience approach to schizophrenia and its onset; 2010 Elsevier; Neuroscience and Biobehavioral Reviews 35 (2011); pp. 1644-1653. (Year: 2010).*

Qi, Z. et al.; Computational Modeling of Synaptic Neurotransmission as a Tool for Assessing Dopamine Hypotheses of Schizophrenia; Pharmacopsychiatry 2010: 43 (Suppl. 1); pp. 550-560. (Year: 2010).*

Qi, Zhen et al.; Mathematical Models in Schizophrenia; 2011 Springer; Hanbook of Schizophrenia Spectrum Disorders, vol. 1: Conceptual Issues and Neurobiological Advances, Chapter 14; pp. 305-325. (Year: 2011).*

* cited by examiner

SYSTEMS AND METHODS FOR MODELING AND PREDICTING EFFECTIVE TREATMENTS FOR SCHIZOPHRENIA AND OTHER DISORDERS

CROSS-REFERENCES TO RELATED APPLICATIONS

This application is based on, claims priority to, and incorporates herein by reference in its entirety, U.S. Provisional Application Ser. No. 62/088,024, filed Dec. 5, 2014, and entitled "Systems and Methods for Treating Schizophrenia."

STATEMENT REGARDING FEDERALLY SPONSORED RESEARCH

This invention was made with government support under K08MH072771 and P50MH060450 awarded by the National Institute of Health. The government has certain rights in the invention.

BACKGROUND

The disclosure relates generally to systems and methods for treating schizophrenia and, more particularly, to systems and methods for modeling and predicting effective treatments, including drug treatments for schizophrenia.

The global burden of major neuropsychiatric illnesses, such as schizophrenia, bipolar illness, major depression, and Alzheimer's disease, is immense (World Health Organization 2001), owing both to the chronic and highly debilitating nature of these conditions and to their relatively high prevalence (Kessler et al. 2005). Current pharmacologic treatments for these diseases vary in efficacy, with most being incompletely effective, and many carrying significant side effect burdens (J. T. Coyle et al. 2010). Despite considerable amounts of psychopharmacologic research in recent decades, no agents with fundamentally new mechanisms of action have been identified, and by most accounts, there is little to speak of in the developmental pipeline (Nestler and Hyman 2010). This is particularly glaring in light of the explosion of neuroscience research over the past ten to twenty years—this work has led to a vast body of knowledge on the neurobiological correlates of many of these conditions, but this had sadly not led to the breakthrough medications that had been anticipated.

One possible reason psychiatry has lagged other medical specialties in arriving at more effective treatments is that the field has focused on clinical phenomenology, rather than etiology, to define illnesses—an important constraint, given the lack of understanding of underlying cause of most psychiatric diseases. Indeed, currently psychiatric illnesses are defined by particular constellations of signs and symptoms, as detailed in the Diagnostic and Statistical Manual of Mental Disorders (DSM-5) (American Psychiatric Association 2013). Thus, a drug trial for the treatment of depression, for example, may include a highly heterogeneous group of patients from the point of view of underlying biological processes (Singh and Rose 2009). Over the past ten or so years, however, there has been a sea change in the manner in which researchers are attempting to understand psychiatric illnesses, with a new emphasis on the use of rigorously defined biological markers, or biomarkers, rather than clinical impression alone (Miller 2010). A biomarker is defined as "a characteristic that is objectively measured and evaluated as an indicator of normal biological processes, pathogenic processes, or pharmacologic responses to a therapeutic intervention." (Biomarkers Definitions Working Group 2001). Thus, biomarkers lie at an intermediate level, between biological and genetic underpinnings and clinically observable symptoms—as such, focusing on these readouts may be a more fruitful way forward, both in terms of categorizing psychiatric illness (Casey et al. 2014) and arriving at more effective and targeted treatments (Meyer-Lindenberg and Weinberger 2006). In recent years, a number of biomarkers for several central nervous system (CNS) disorders have been proposed (Perlis 2011).

The clear technical difficulties in accessing and manipulating the human brain at the neural level have made it necessary, practically speaking, to instantiate biomarkers of psychiatric illness in an in vivo or in vitro manner as pharmacologic test systems. Often these involve developing biomarker-based assays in rodents and assessing potential medications' ability to affect these measures. However, this approach can present problems, for a number of reasons. First, the dysfunction characteristic of the disorders in question—e.g., the paranoid delusions seen in schizophrenia, the extreme dysphoria associated with depression—may, in many ways, be uniquely human. Part and parcel of this disconnect is that rodent, and even non-human primate brains are not strictly analogous with human brains, and these dissimilarities could be very significant in terms of these illnesses. The prefrontal cortex (PFC), for example shows marked increases in size and complexity as one ascends the evolutionary ladder (Ongur and Price 2000; Defelipe 2011). Also, while animal models are certainly more manipulable and query-able in comparison with humans, in these model systems, the rodent brain still remains a "black box," whose workings, at a mechanistic, causal level, are by no means transparent.

With the historical emphasis on in vitro and in vivo animal models of psychiatric illness, the potential for computational, or in silico, models to help develop pharmacologic treatments for these conditions has remained largely untapped. One research group has outlined a process for using computational approaches to screen candidate psychiatric medications—that is, to evaluate the potential efficacy and side effect burden of existing candidate agents, based on their affinity at known neurotransmitter receptors (Geerts et al. 2012). This could potentially play a role at one point in the drug development process, when a putative agent has been characterized molecularly, and its effects on known receptors have been analyzed and quantified. However, such a construct limits the ability to develop truly novel agents.

Therefore, a need persists for systems and methods that enable researchers and clinicians to model and predict effective treatments for schizophrenia and other disorders.

BRIEF SUMMARY

The present disclosure provides systems and methods for modeling schizophrenia and other disorders as a combination of N-methyl-D-asparate (NMDA) deficit, decreased connectivity, and hyperdopaminergia. These model parameters may be weighted differently and provide reports indicating drug or other therapeutic options or combinations that maybe effective.

In accordance with one aspect of the disclosure, a computer system is provided that includes a non-transitory memory having stored thereon a model for a psychological condition and a control model and having instructions for evaluating an effectiveness of a therapy for a psychological condition. The computer system also includes a processor configured to access the memory and carry out steps. The steps include (i) selecting a therapy to be analyzed and (ii) applying the therapy selected in step (i) to the model of the psychological condition, wherein the model includes hyperdopaminergia as a function. The steps also include (iii) determining a response using an output of step (ii), (iv) comparing the response to the control model to determine a wellness metric, and (v) generating a report indicating an effectiveness of the therapy based on the wellness metric.

In accordance with another aspect of the disclosure, a method is provided for evaluating an effectiveness of a therapy for a psychological condition. The method includes steps of (i) selecting a therapy to be analyzed relative to psychological pathology and (ii) applying the therapy selected in step (i) to a model of the psychological condition that includes hyperdopaminergia as a function in the model. The method also includes steps of (iii) determining a response using an output of step (ii), (iv) comparing the response to a control to determine a wellness metric, and (v) generating a report indicating an effectiveness of the therapy based on the wellness metric.

In accordance with yet another aspect of the disclosure, a method is provided for evaluating an effectiveness of a drug for treating a psychological condition. The method includes selecting a drug to be analyzed relative to psychological pathology and applying the therapy selected to a testing construct related to the psychological condition. The method also includes generating a report indicating a positive effectiveness of the drug upon determining one of the following: causing a decrease in a decay time constant of an alpha2 receptor (alpha2tau2); causing a decrease in a decay time constant of an alpha2 receptor (alpha2tau2) in combination with increasing generalized γ-aminobutyric acid (GABA) conductance; causing a decrease in a decay time constant of an alpha2 receptor (alpha2tau2) in combination with decreasing AMPA synapse decay time constant (AMPAtau2); causing a decrease in a decay time constant of an alpha2 receptor (alpha2tau2) in combination with increasing CR cell projection strength; causing a decrease in AMPA synapse decay time constant (AMPAtau2); causing a decrease in AMPA synapse decay time constant (AMPAtau2) in combination with increasing CR cell projection strength; causing increasing generalized γ-aminobutyric acid (GABA) conductance in combination with decreasing AMPA synapse decay time constant (AMPAtau2); causing increasing generalized γ-aminobutyric acid (GABA) conductance in combination with increasing N-methyl-D-aspartate (NMDA) conductance; or causing increasing generalized γ-aminobutyric acid (GABA) conductance in combination with increasing CR cell projection strength and increasing N-methyl-D-aspartate (NMDA) conductance.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF DRAWINGS

The patent or application file contains at least one drawing executed in color. Copies of this patent or patent application publication with color drawing(s) will be provided by the Office upon request and payment of the necessary fee.

The invention will be better understood and features, aspects and advantages other than those set forth above will become apparent when consideration is given to the following detailed description thereof. Such detailed description makes reference to the following drawings.

DETAILED DESCRIPTION

Figure 1:
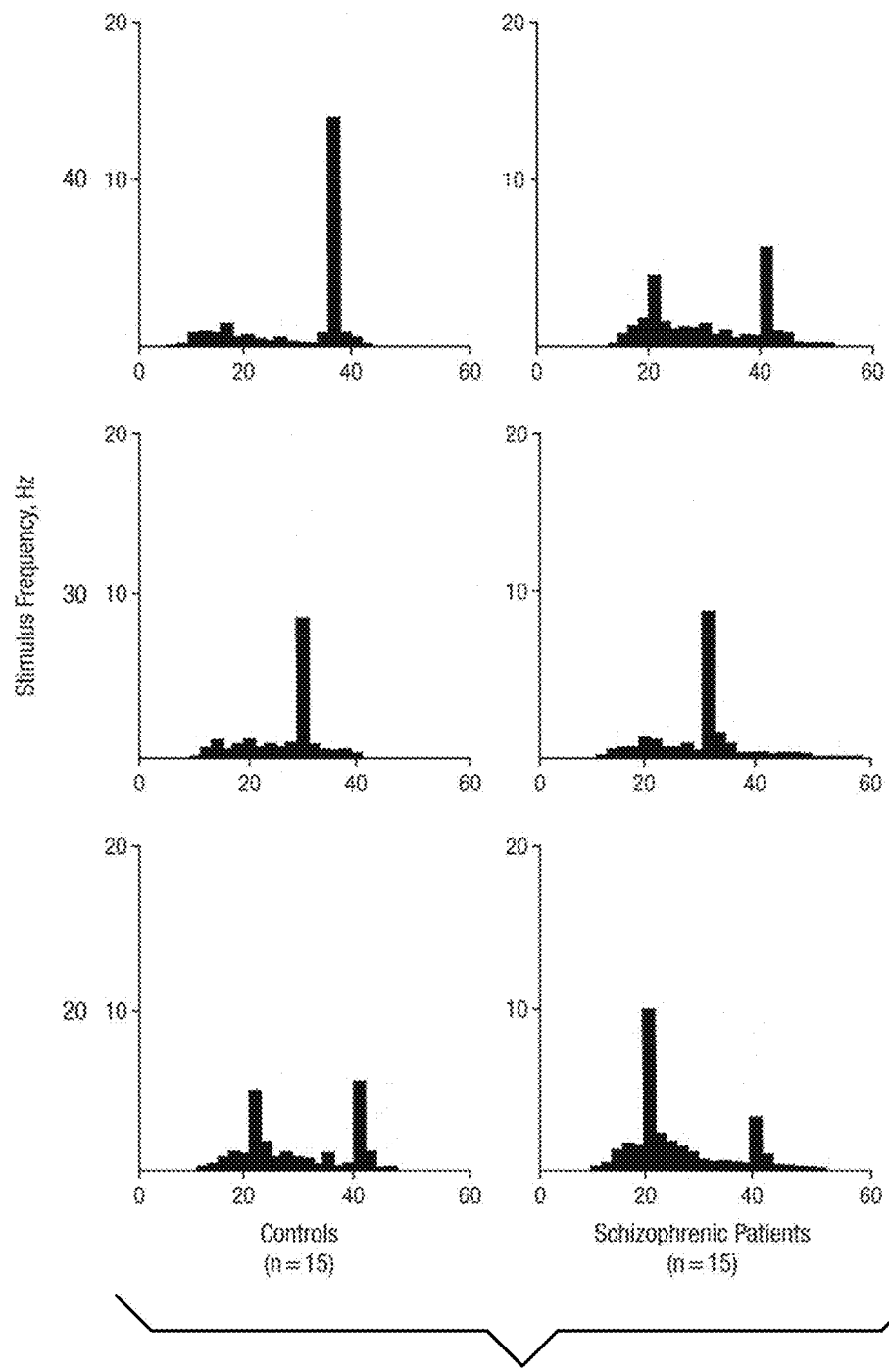
FIG. 1 is a series of correlated graphs showing Brain oscillatory activity from clinical electroencephalographic (EEG) studies. Control subjects (left panels) and schizophrenic subjects (right panels) were exposed to auditory click trains at 20, 30, and 40 Hz. Resultant EEG power spectra are shown.

As will be described, the present disclosure provides specific operationalization of a generalized method of using biophysically realistic biomarker-based computational models to identify novel candidate medications for neuropsychiatric illness. While schizophrenia is used as a non-limiting example, given that it has strong heritability and clear biological roots, and has received particular attention in the biomarker literature, the systems and methods described herein are not limited to schizophrenia, but can be used for other psychological disorders, such as autism, fragile-X syndrome, and Alzheimers disease, which include identifiable biomarkers, as well as bipolar disorder, depression, obsessive-compulisve disorder, and substance abuse. Schizophrenic patients have demonstrated specific deficits in their ability to attune to gamma band (40 Hz) auditory stimuli. This can be used as our biomarker, as it is a readily measurable, quantifiable outcome metric that is, according to multiple clinical studies, characteristic of the schizophrenia and may underlie important aspects of disease symptomatology. However, corollary biomarkers associated with other disorders can be substituted when considering such disorders. With respect to this example biomarker for schizophrenia, the biomarker can be used in a detailed tissue-level computational model of hippocampus that is rendered schizophrenic by the inclusion of neuroanatomic and neuropsychological abnormalities that are felt to underlie the illness, based on large amounts of recent basic experimental research. The diseased model can be exposed to "virtual medications" or other "virtual therapies" to determine a projected likelihood of success for a given therapy or therapies or to recommend particular therapies for consideration by a clinician.

More particularly, as will be described, present disclosure provides systems and methods for modeling schizophrenia and other disorders as a combination of functions including NMDA deficit, decreased connectivity, and hyperdopaminergia, which is distinguished from models that only consider schizophrenia as a deficit in NMDA receptor functioning and decreased neural connectivity. As will be described, this distinction recognizes that currently-used antipsychotics are generally dopamine (DA) antagonists. While some drugs, particularly the newer so-called atypical antipsychotics, act at other receptor sites as well, it is felt that DA blockade is central to these drugs' efficacy. However, the present disclosure recognizes that significant problems exist with these drugs because they can lead to serious and potentially irreversible side effects, and they are not effective for all patients. Thus, as will be described, a system and method are provided to identify medications that may be able to counteract the effect of DA, but through non-dopaminergic mechanisms.

1. Methods

1.1 Background: Oscillatory Abnormalities in Schizophrenia

Past research on the etiology of schizophrenia has tended to focus on abnormalities in particular circumscribed brain areas, such as basal ganglia or PFC, or center on the presumed dysregulation of particular neurotransmitters, such as DA. Over the past several years, there has been an increased appreciation that schizophrenic symptomology may arise from deficits in neural synchrony (Uhlhaas and Singer 2015). This is not surprising, as it is possible that oscillatory activity at various frequencies may be a mechanism by which temporal relationships between ensembles of neurons are established. It is hypothesized that this is key in subserving normal cognition, and there is a growing body of literature on how this may go awry in schizophrenia (Pittman-Polletta et al. 2015). This work has looked at discrete deficits in particular frequencies, such as the delta (1-4 Hz), theta (4-7 Hz), alpha (8-13 Hz), beta (13-30 Hz) bands, or the gamma range, defined as ranging from 30 Hz, to as high as 50 or 80 Hz (Hughes 2008). Increasingly, deficits in coordination between different frequency bands, in the form of cross-frequency coupling (in which the phase of the slower frequency band modulates the amplitude of the faster one) have also been seen in the illness (Moran and Hong 2011).

In a recent review of the literature of oscillatory abnormalities in schizophrenia, Uhlass & Singer (2010) examined not only frequency band, but various task paradigms under which they can be elicited. For example, the examination included oscillations that are evoked by a particular discrete stimulus, and thus time-locked to it; induced activity; steady state evoked potentials; and resting, or spontaneous, activity. They found that across all of these testing paradigms, and over all frequencies examined (delta through gamma), the deficit with the most robust evidence in the literature was the following: schizophrenia patients showed decreased amplitude in steady state evoked potentials in the gamma frequency band, as compared with controls.

Typically, steady state evoked potentials are elicited using the auditory steady state response (ASSR) task. In this testing paradigm, the subject is exposed to trains of clicks or tones, via headphones, at a number of frequencies, such as 20, 30, and 40 Hz; during these trials an electroencephalogram (EEG) is recorded. Under these conditions in control subjects, spectral analysis of EEG activity shows greatest power at the stimulated frequency. However, schizophrenic patients depart from this pattern, and show a unique inability to attune to 40 Hz (gamma band) activity. An example of a study exhibiting this effect (Kwon et al. 1999) is shown in FIG. 1. This effect has been replicated multiple times in both EEG (e.g., Teale et al. 2008; Wilson et al. 2008; Light et al. 2006; Krishnan et al. 2009; Spencer et al. 2008) and magnetoencephalographic (MEG) (Tsuchimoto et al. 2011) studies, and it has been argued (Gandal et al. 2012) that this may represent a sensitive and specific biomarker for the illness.

1.2 Model

Attempts to understand DA's effects on hippocampal functioning in a detailed, mechanistic way—and how this may go awry in schizophrenia—are made complicated by two considerations. First, it has become clear that DA affects neural processing not through a single electrophysiologic effect, but through a broad range of activities on synaptic and ion channel functioning. Second, recent research has made abundantly clear that other neurotransmitters—e.g., the glutamatergic and GABAergic systems—are abnormal in hippocampus in schizophrenia. Additionally, aberrant connectivity has also been seen. A priori, it is not clear how DA deficiencies would interact with these abnormalities.

As will be addressed, the present disclosure provides systems and methods that address these issues using a systems biology approach. As described in detail in previous work (P. J. Siekmeier 2009), we have created a detailed biophysically realistic model of hippocampus, consisting of 160 pyramidal cells, 60 parvalbumin-positive (PV+) interneurons (30 basket cells and 30 chandelier cells), and 20 calretinin-positive (CR+) interneurons. For pyramidal cells, and interneurons, we used the 64-compartment model of Traub et al (1994) and the 46-compartment model of Traub & Miles (1995) respectively, both of which included realistic dendritic arbors, as well as $Na^+$, $Ca^{2+}$, $K^+_{DR}$, $K^+_{AHP}$, $K^+_C$ and and $K^+_A$ channels with Hodgkin-Huxley dynamics.

This model can be further augmented to create a biophysically detailed computational hippocampal model (Siekmeier and vanMaanen, 2013) implemented on a 72 processor supercomputer, and take a specific quantitative deficit in the 40 Hz auditory steady state response (ASSR) as index of schizophrenic behavior. One example is provided in co-pending U.S. patent application Ser. No. 13/915, 413, filed Jun. 11, 2013, and incorporated herein by reference in its entirety for all purposes.

In particular, we modified these by the inclusion of N-methyl-D-asparate (NMDA), α-amino-3-hydroxy-5-methyl-4-isoxazolepropionic acid (AMPA), and γ-aminobutyric acid (GABA) channels with realistic temporal dynamics, as well as simulated DA receptors, which incorporate the effect of dopamine in a concentration-dependent manner via its effect on synaptic activity and intrinsic ion channel behavior (as detailed in Siekmeier & vanMaanen (2014)).

Connectivity was based on an exhaustive review of the neuroanatomic literature. To simulate auditory click trains, we delivered stimulatory drive to the constituent pyramidal cells and interneurons of model in a manner designed to simulate thalamic inputs (Vierling-Claassen et al. 2008). We drove the model at 20, 30, and 40 Hz, in order to replicate the frequencies generally used in the clinical literature, and recorded a simulated EEG using a virtual electrode which integrated electrical activity across all cells in the model using the Nunez equation (Nunez 1981).

Thus, the overall DA effect can interact with other abnormalities, including GABA and NMDA, and other potential schizophrenegic neuropathologies. Accordingly, as disclosed herein, DA effects are applied via alterations in a constellation of synaptic and ion channel effects, in a receptor mediated manner, both to an unaffected (control) and a schizophrenic model. In the schizophrenic model, increasing DA levels leads to a decrement in gamma band response. In the control model, similar DA levels show a modest enhancement of gamma band activity (similar to experimental work). These new models, the dynamics of these models, and strategies for using these models are provided and have implications for the development of novel agents to treat schizophrenia.

1.2.1 Model Construction

In the auditory steady state response (ASSR) task, subjects receive auditory stimuli (generally by earphones) at various frequencies, and cortical response is measured via electroencephalography (EEG) or magnetoencephalography (MEG). Typically, frequencies that are presented in the response signal are determined via Fourier transform or wavelet analysis. Stimulation protocols include a range of frequencies (e.g., 20, 30, and 40 Hz), and generally control subjects show a strong cortical response at the stimulated frequency. Schizophrenic patients, however, show a unique inability to attune to gamma band (approximately 40 Hz) stimulation—multiple studies have shown that schizophrenic patients' 40 Hz response to 40 Hz drive is markedly lower than that of controls, whereas response at other frequencies (e.g., 20 and 30 Hz) is comparable to those of controls. Oscillatory abnormalities in a number of frequency bands (delta [1-4 Hz], theta [4-8 Hz], alpha [8-12 Hz], beta [12-30 Hz], and gamma) have been identified in schizophrenia. Across all experimental protocols, the most robust effect was found in patients in the gamma band ASSR task. Thus, this may be used as a biomarker reflective of a key neural deficit in schizophrenia.

A new computational model is created that may be driven, for example, at 20, 30, and 40 Hz. That is, the input stimulation may be delivered to the computational neurons of the model, in a manner detailed in the aforementioned simulation (Siekmeier and vanMaanen, 2013) and described in co-pending U.S. application Ser. No. 13/915,413, filed Jun. 11, 2013. This is meant to emulate the auditory stimuli employed in the experimental human studies using the ASSR task, at the frequencies most commonly used. For each run, a simulated EEG is written to file. Two distinct network models can be used. One network model corresponds to the control case and the other corresponds to the schizophrenic case. The control model is tuned to show similar 20, 30, and 40 Hz behaviors to the controls in experimental studies. The schizophrenic model is created by searching the parameter space of putative schizophrenic neural abnormalities (in NMDA function, GABA system integrity, and dendritic spine density), using the response to the ASSR task as a key outcome metric. Compared to the control model, the schizophrenic model has a 30% decrease in NMDA conductance and a 30% decrease in dendritic spine density, and also has increased dopamine levels.

The model can be implemented using the General Neural Simulation System (GENESIS) neural modeling software (Bower and Beeman, 1998),version 2.3, with MPI programs written in C++ for parameter searches. One hardware platform used a 72 processor dedicated Beowulf Cluster running under Linux (Red Hat Enterprise Linux 5.0). The backward Euler integration method as implemented in standard GENESIS is used as a differential equation solver, with a 0.1 ms time step; this provided sufficient accuracy while still allowing manageable processing speeds for the simulations described. A 1.5 second "neuron time" simulation takes approximately 1.5 hours to complete on one processor.

1.2.1.1 Inclusion of Schizophrenogenic Neuropathology

The etiology of schizophrenia at the cellular level is not known with certainty. This is an extremely active area of research, and over the past several years a number of neuroanatomic and neurohumoral deficits have been identified, which broadly fall into four categories, as follows: (a) NMDA system deficits. A large body of research literature suggests that NMDA receptors of schizophrenic patients' brains show a decrease in number, or decreased functionality, or both; see Coyle (2006) for a review of this work. NMDA receptor subtypes residing on particular subcategories of interneurons may be of particular importance (Kirli et al. 2014; Jadi et al. 2015). (b) Connectivity disturbances. Considerable evidence exists that there is disturbed neuron-to-neuron connectivity in schizophrenia brain, possibly as an upshot of overpruning of neurons in the course of development (Hoffman and McGlashan 2003; Feinberg 1982), and as manifested in post-mortem studies that have revealed decreased dendritic spine density in schizophrenic pyramidal neurons (e.g., Law et al. 2004; Garey et al. 1998). (c) GABA system dysfunction. A vast body research indicates there may be a decrease in GABAergic activity in the brains of schizophrenic patients (e.g., Fatemi et al. 2000; Torrey et al. 2005; Heckers et al. 2002); additional work has shown a (possibly compensatory) upregulation of post-synaptic GABA receptors (Benes et al. 1996; Lisman et al. 2008). This work is thoroughly reviewed in Benes & Baretta (2001). (d) Dopaminergic dysfunction. Some research suggests excessive DA levels may contribute to schizophrenic symptomatology (Howes et al. 2012). This is consistent with the fact that all currently used antipsychotic medications block dopamine. However, models have not considered such.

The computational model of schizophrenic hippocampus used in the studies described herein incorporates a combination of the aforementioned neural-level lesions. To arrive at this model required extensive research and discovery. In brief terms, the control (i.e., non-diseased) model described in Section 1.2 above was created. Studying this model, we found that a model with decreased dendritic spine density (−30% compared with the control mode), decreased NMDA functionality (−30% compared with control), and increased DA concentration (31 μm over control) showed oscillatory behavior on the simulated ASSR task nearly identical to that seen in clinical studies. Specifically, it demonstrated a decrease in 40 Hz response of 26% compared with control, and no appreciable difference in 20 or 30 Hz response. While there is no consensus in the literature on the precise percentage deficit that exists in schizophrenic gamma band ASSR, one example that may be used is the experimental EEG work of Teal et al (2008). This group carried out detailed source localization, which indicated the oscillatory activity, and deficit, lay in the temporal lobe, and may be hippocampal in origin.

1.2.1.2 Operationalization of Dopaminergic Effects

At baseline in humans, extracellular dopamine levels are understood to be around 10-20 nM, and with activity, intrasynaptic concentrations can reach the micromolar range. Direct measures of tissue level increases of DA in schizophrenic patients are, of course, very difficult to obtain. Indirect measures involving [$^{11}$C]raclopride binding or CSF samples have tended to show modest DA increases in patients. To ensure that any possible effect is captured, the model can account for DA increases ranging over several orders of magnitude, for example, from 0 to 1 mM.

Dopamine effects are mediated cellularly via G-protein coupled dopamine receptors, which can broadly be divided into the D1-like receptors (D1 and D5) and the D2-like receptors (D2, D3, and D4). Human postmortem studies that have done direct comparisons have shown that D1 receptors outnumber D2 receptors in hippocampus, and indicated that this difference is considerable. For example, some have showed that in CA1, D1 density, as measured by [$^3$H] SCH23390 binding, was 30.03 fmol/mg tissue, whereas D2 density, as measured by [$^{125}$I]Epidepride binding, was 0.18 fmol/mg tissue, a 17-fold difference. Additionally D1 vs. D2 binding has been assed in postmortem human brain using homogeneous (that is, not subfield specific) samples from hippocampus, and found average D1 concentrations of 1.4 pmol/g, vs. negligible concentrations of D2 receptors. The ratio of D1 to D2 receptors in human hippocampus has been estimated at approximately 11 to 1. Therefore, the model can focus or be weighted toward on D1-type receptor mediated effects. Also, data from trials using D1-like agonists were used to calculate $E_{max}$ values, as will be described.

There is an extensive literature on the manner in which DA exerts neurophysiologic effects by altering ion channel and synaptic conductances. For example, this research has shown that DA and DA agonists significantly decrease conductance of the $K_{AHP}$ and $K_C$ channels, increase conductance at AMPA synapses, and have small or negligible effects at the $K_{DR}$ and $K_A$ channels.

As described below, DA effects can be introduced into the model in a concentration dependent manner. Assume that the fraction of DA receptors bound is a function of DA concentration and its dissociation constant at the DA receptor, $K_i$, as follows:

$$P=[DA]/[DA]+K_i \quad \text{Eqn. 1}$$

Here, P is the percentage of DA receptors bound. We take $K_i$ to be, for example 4.3, (expressing the dissociation constant as the negative exponent of the concentration, in molar terms, at which 50% of receptors are occupied). Assume that the ultimate neurophysiologic effect (e.g., increase or decrease in ion channel conductance, expressed as $E_A$ below) is a linear function of DA receptor occupancy, as given by:

$$E_A=E_{max} \times P \quad \text{Eqn. 2}$$

The proportionality constant $E_{max}$ is different for each distinct ion channel or synapse. These values were derived from experimental studies that quantified the change in channel conductance when tissue was exposed to particular concentrations of DA or DA agonist. $E_{max}$ values and the experimental studies from which they were derived, are shown in Table 1. Each study noted herein is incorporated herein by reference in its entirety.

TABLE 1

| Channel | $E_M$ | Source |
| --- | --- | --- |
| Na$^+$ | −22.2% | Cantrell et al (Cantrell et al, 1997) |
| Ca$^{++}$ | −20.0% | Surmeier et al (Surmeier et al, 1995) |
| $K_{DR}^+$ | 0.0% | Dong and White (Dong et al, 2003) |
| $K_{AHP}^+$ | −35.9% | Pedarzani and Storm (Pedarzani et al, 1995) |
| $K_C^+$ | −48.1% | Sataki et al (Sataki et al, 2008) |
| $K_A^+$ | −24.5% | Dong and White (Dong et al, 2003) |
| NMDA | −33.6% | Castro et al (Castro et al, 1999) |
| AMPA | +5.0% | Yang (Yang, 2000) |
| GABA$_A$ | −23.0% | Liu et al (Liu et al, 2000) |

1.2.1.3 Review of Model

Figure 2A:
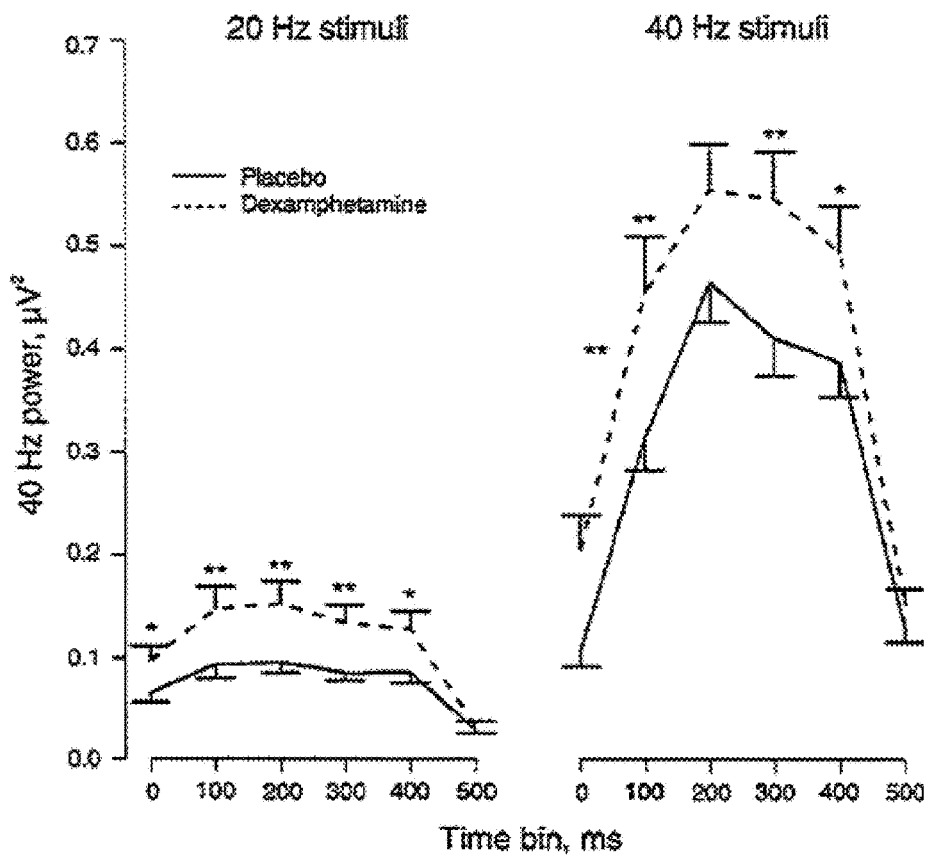
FIG. 2A is a graph showing findings of Albrecht et al (2013), in which subjects were exposed to 20 Hz and 40 Hz stimuli. Bars indicate standard error.

To confirm the validity of the control model, its behavior was quantitatively compared to that observed in clinical studies. Albrecht et al (2013) studied 44 unaffected (non-schizophrenic) subjects using the ASSR task, with 20 Hz and 40 Hz stimulation. In one trial, subjects were given dexamphetamine, to induce hyperdopaminergia, and in the other, they received placebo. They used an experimental protocol in which stimuli (20 Hz or 40 Hz click trains) were presented for 500 ms, with 500 ms interstimulus intervals, and they found that when treated with dexamphetamine, subjects showed a significantly greater 40 Hz response to 40 Hz stimulation, and also significantly greater 40 Hz response to 20 Hz stimuli (FIG. 2A). When we carried out their experiment computationally—by stimulating with background noise for 500 ms, then driving the model as described above for 500 ms, then delivering background noise—we achieved similar results (FIG. 2B).

Figure 2B:
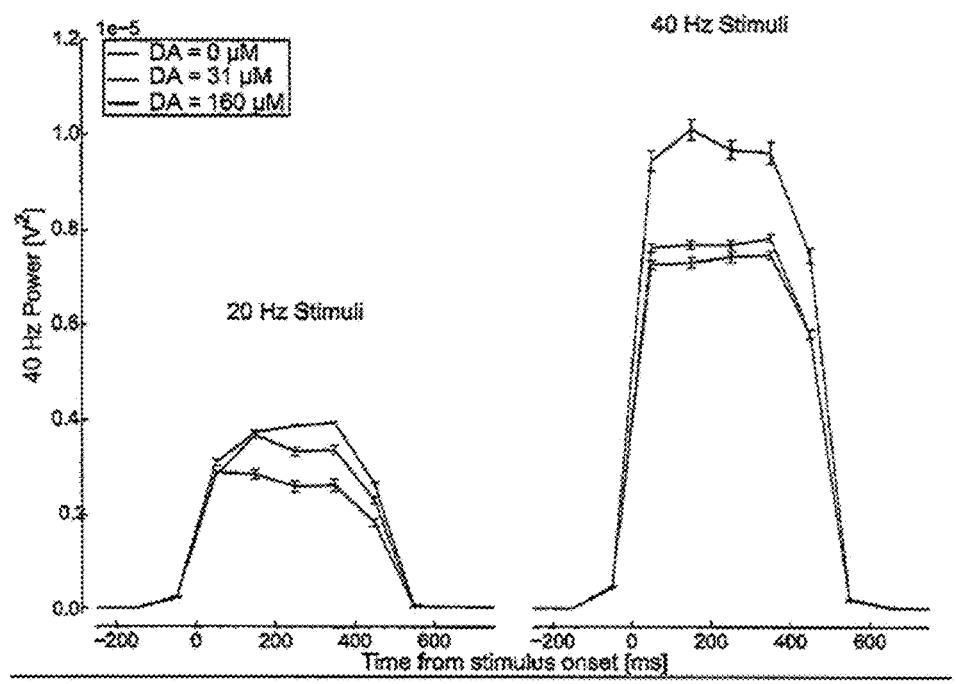
FIG. 2B is a graph showing experimental findings from computational model outputs for analogous task.

More particularly, FIGS. 2A and 2B illustrate data from auditory steady state response (ASSR) task in control subjects for experimental vs. computational results. Because it is not entirely clear how dexamphetamine dosage used by Albrecht et al (0.45 mg/kg) would translate quantitatively to serum level, we used a range of DA concentrations. Response power at 40 Hz is shown on y-axis. Input drive lasted 500 ms (as in clinical experimental task), and x-axis indicates time from onset of this stimulus. Data are binned at 100 ms. Bars indicate standard error.

1.3 Incorporating Virtual Medications 1.3.1 Approach

A premise underlying the drug discovery methodology described herein is that the relevant "target" is not a discrete neurobiological entity, but rather a system-level behavior. The metric for judging the potential efficacy of a virtual pharmacologic agent is its ability to return the schizophrenic pattern of oscillatory behavior on the ASSR task at 20, 30, and 40 Hz to the baseline (i.e. unaffected) pattern—i.e., its ability to normalize the system. This should be contrasted to many past drug discovery approaches, in which the target is a particular discrete neural element such as a receptor, and the object is to identify an agent that interacts with it as an agonist or antagonist.

With this in mind, the selection of the specific effects that were chosen to be examined were not exhaustive. That is, the particular set of neurobiological alterations we look at below is not meant to be exhaustive. Rather, the purpose is to illustrate the implementation of a parameter search based drug discovery methodology using a manageable number of effects. Clearly, as effects (dimensions) are added, the parameter space grows exponentially—which can make for unmanageably long runs even on our supercomputer platform. Also, the computational model is, like the brain tissue it is designed to model, a highly complex system. As such, microscopic changes can interact in highly non-linear ways in their impact on macroscopic (system level) behavior in ways that are very difficult to predict a priori.

1.3.2 Specification of Cellular Level Effects

To the schizophrenic computational model described above, we applied the effects of 2,000 "virtual drugs." We did so using five cellular level simulated medication effects, applying each to the model individually, and in combination. In other words, we searched the parameter space of these effects, performing runs in which we incorporated the following alterations (as summarized in Table 2). That is, Table 2 provides a summary of parameter search methodology for simulated medication effects. Each of the effects in the "Parameter" column was varied through the range of values indicated, alone and in combination with all other effects. Total number of parameter sets (or simulated medications), is 4×4×5×5×5=2,000.

TABLE 2

| Parameter | Description | Units | Range of Values |
|---|---|---|---|
| GABA cond | conductance of GABA channel (generalized GABA activity) | % increase | 0, 10, 20, 30 |
| $\alpha_2 \tau_2$ | decay time constant of GABA synapse, $\alpha_2/\alpha_3$ subtype | % decrease | 0, 25, 50, 75 |
| NMDA cond | conductance of NMDA channel | % increase | 0, 20, 40, 60, 80 |
| AMPA $\tau_2$ | decay time constant of AMPA channel | % decrease | 0, 16.7, 33.3, 50, 66.7 |
| CR proj | weight of projection of CR+ cells on postsynaptic targets | % increase | 0, 10, 20, 30, 40 |

Total number of simulated medications: 2,000

1.3.2.1 Increased GABA Activity

The benzodiazepines (which include lorazepam [Ativan], diazepam [Valium], and clonazepam [Klonopin], among others), are GABA receptor agonists. While there is not consistent evidence that these agents are effective in treating schizophrenia as maintenance agents, they are commonly used in combination with other drugs for acute psychotic exacerbations in schizophrenic patients (Labbate et al. 2010). Because these affect GABA activity generally (that is, irrespective of the site of the GABA receptor), we incorporated this effect by increasing the conductance of GABA channels across the board, in four gradations (conductance increase of 0, 10, 20, and 30%).

1.3.2.2 Increased NMDA Conductance

As evidence grew that dysfunction of the glutamate system may be involved in schizophrenia, a number of clinical trials using NMDA agonists and co-agonists (e.g., D-[serine]) were undertaken, with mixed results (Nunes et al. 2012). Such drugs could be ameliorative, both via a direct effect—increasing conductance of the NMDA channel—and a second order effect of boosting LTP, as this occurs via the NMDA synapse (Shouval et al. 2002). To include these effects, we increased conductance at the NMDA channel in five gradations (baseline, and increases of 20, 40, 60, and 80%).

1.3.2.3 Decreased Decay Time Constant ($\tau_2$) of the AMPA Synapse

As part of a previous modeling study, we manipulated the time constant of the (excitatory) AMPA channel, and found that this had a beneficial effect on schizophrenic model behavior. Exploratory runs indicated there was a high level of sensitivity to changes in this parameter value. Therefore, we decreased this in 5 gradations (baseline, and decreases of 16.7, 33.3, 50, and 66.7%).

1.3.2.4 Decreased the Decay Time Constant ($\tau_2$) of the $\alpha_2/\alpha_3$ GABA Receptor Subtype In previous computational modeling work, Vierling-Claassen et al. (2008) showed that increasing the time constant of a particular interneuron projection—specifically, the (inhibitory) projection of PV+ chandelier cells, which impinge on the initial segment of pyramidal cells—has a strongly schizophrenogenic effect, when using decreased 40 Hz ASSR as a marker for the illness. Also, a large body of post-mortem and other experimental research (e.g., Woo et al. 1998) has suggested this particular synapse is involved in the pathogenesis of schizophrenia. Based on these two considerations, we decreased the decay time constant ($\tau_2$) of the $\alpha_2/\alpha_3$ GABA receptor in our model in four gradations (baseline, and 25, 50, and 75% reductions.)

1.3.2.5 Increased Calretinin Cell Projection Strength

Calretinin interneurons project only to other interneurons, and therefore increasing their activity has a disinhibiting effect, leading to overall increases in oscillatory activity. (We observed this in preliminary exploratory model runs, in which various parameters were modified and effects on the model were observed.) This is a potentially interesting set of neurons, as they have not been implicated in the pathogenesis of schizophrenia, but affecting their output could possibly positively change network dynamics. Therefore, we increased the parameter specifying CR+ cell projection strength in five gradations (0, 10, 20, 30, and 40% increases over baseline.)

1.4 Operation

A "wellness metric" (WM) was established to indicate how closely a treated schizophrenic model approximated the control state, calculated as follows: for each of the 2,000 iterations (each corresponding to a virtual drug) we drove the model at 20, 30, and 40 Hz; a simulated EEG was generated and was analyzed by Fourier transform to determine which frequencies were present. If a model exactly replicated control model 40 Hz behavior, it received a WM score of 1; the score was decreased, to a WM minimum score of 0, to the extent that it departed from this. The parameter $D_{40}$ below represents the deficit in the schizophrenic model's 40 Hz response, at baseline, compared with the control model (thus, $D_{40}$ =26%).

Figure 3:
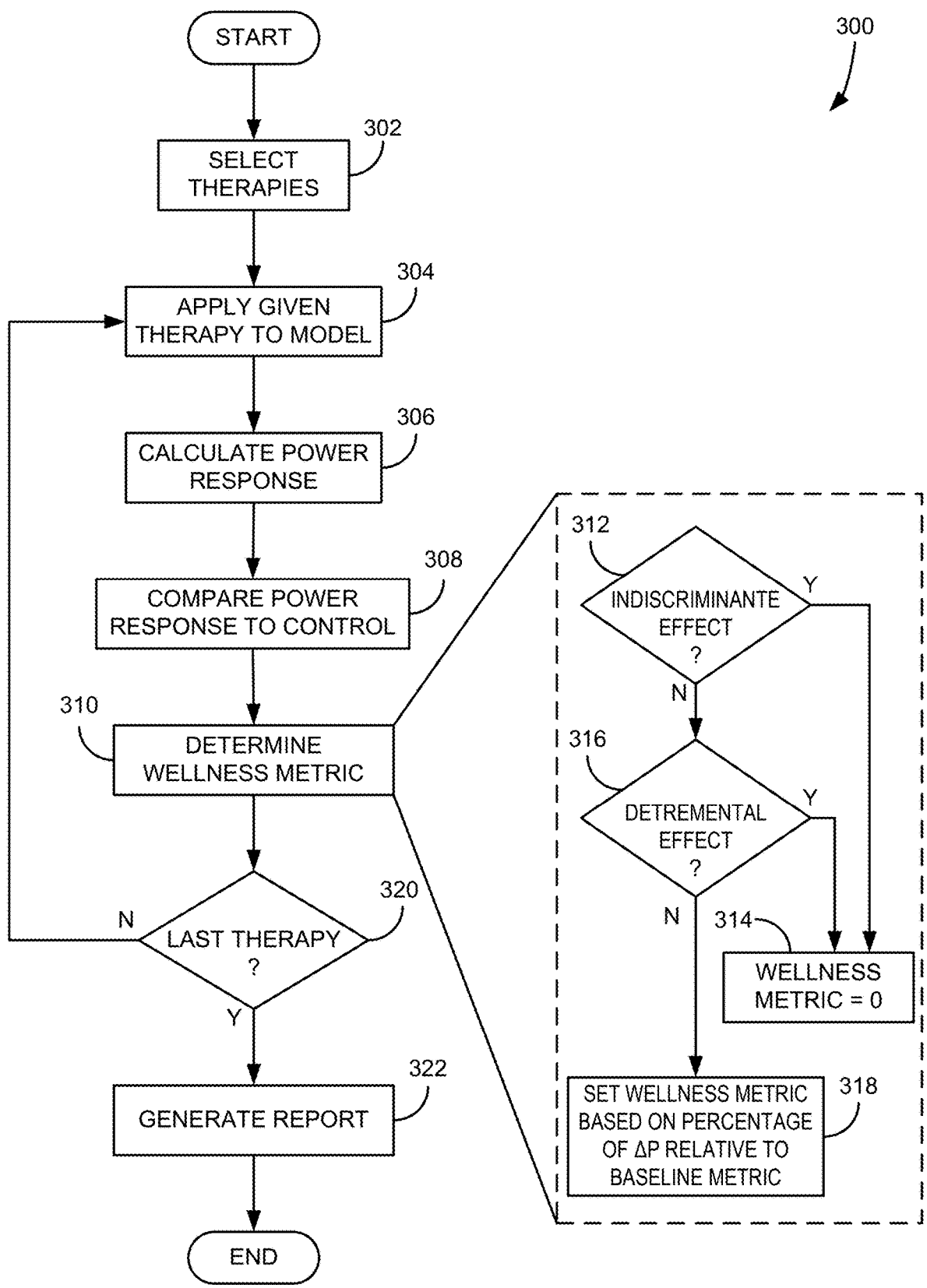
FIG. 3 is a flow chart setting forth some example steps of a method in accordance with the present disclosure.

Referring to FIG. 3, the wellness metric may be used to evaluate the effectiveness of a therapeutic, such as a drug. An example of steps 300 of a process in accordance with the present disclosure begins at process block 302 by selecting desired therapies, such as drugs, to be evaluated. At process block 304, a given therapy of those selected at process block 302 is applied to the above described model, which, unlike traditional models, may model schizophrenia as a combination of functions including NMDA deficit, decreased connectivity, and hyperdopaminergia.

Using the model, at process block 306, a power response is calculated, which is then compared at process block 308 to a power response of a the control. More particularly, for a given therapy to be applied to the schizophrenic model at process block 304, the power of response can be calculated at 20 Hz ($P_{20,s}$), 30 Hz ($P_{30,s}$ and 40 Hz ($P_{40,s}$) and compared to the control.

For example, for each frequency, the percentage difference in the power of response is calculated between the control model (denoted $P_{20,c}$, $P_{30,c}$, and $P_{40,c}$ for 20, 30, and 40 Hz, respectively) and the treated schizophrenic model as:

$$\Delta P_{20} = \frac{P_{20,s} - P_{20,c}}{P_{20,c}}; \quad \text{Eqn. 3}$$

$$\Delta P_{30} = \frac{P_{30,s} - P_{30,c}}{P_{30,c}}; \quad \text{Eqn. 4}$$

$$\Delta P_{40} = \frac{P_{40,s} - P_{40,c}}{P_{40,c}}. \quad \text{Eqn. 5}$$

Using these values of ΔP, a wellness metric can be determined at process block 310. The wellness metric can be calculated a variety of different way to account for different control models or known variations in response to a specific therapy. However, one non-limiting example of a system for calculating a wellness metric is illustrated in FIG. 3. In this non-limiting example, ΔP is evaluated against predetermined criteria.

At decision block 312, a check is made to determine if the given therapy being evaluated had an indiscriminate effect. For example, one method to determine if there was an indiscriminate effect considers whether $|\Delta P_{20}|>10\%$ or $|\Delta P_{30}|>10\%$. If so, the wellness metric for that therapy is set to zero at process block 314. Thus, trials that did not produce 20 and 30 Hz behavior within 10% of control are marked as failed trials, and received a score of zero. This ensures that an agent that, for example, boosted all frequencies indiscriminately was not marked as efficacious.

At decision block 316 another predetermined criteria is evaluated. In this case, the results are analyzed to determine if there was a detrimental effect. For example, one method to determine if there was a detrimental effect considers whether $|\Delta P_{40}|>D_{40}$. If so, the wellness metric is set to zero at process block 314. Therefore, if the treated schizophrenic model is worse than untreated schizophrenic model in terms of gamma band response ($\Delta P_{40} < -D_{40}$), the therapy is scored as zero. Also, if treated schizophrenic model shows supraphysiological resonance at that frequency, which we took to be $\Delta P_{40} > D_{40}$, the therapy was scored as zero.

Then, at process block 318, any cases that remain are used to calculate a wellness metric based on a percentage of ΔP relative to baseline. For example, this can be done as:

$$WM = 1 - \left(\frac{1}{D_{40}} \times |\Delta P_{40}|\right). \quad \text{Eqn. 6}$$

Once the value of the wellness metric for a given therapy is determined at process block 310, at decision block 320, the process iterates for each selected therapy until the last therapy is evaluated using the model. Once all therapies have been evaluated, a report can be generated at process block 322, such as will be described.

Figure 4:
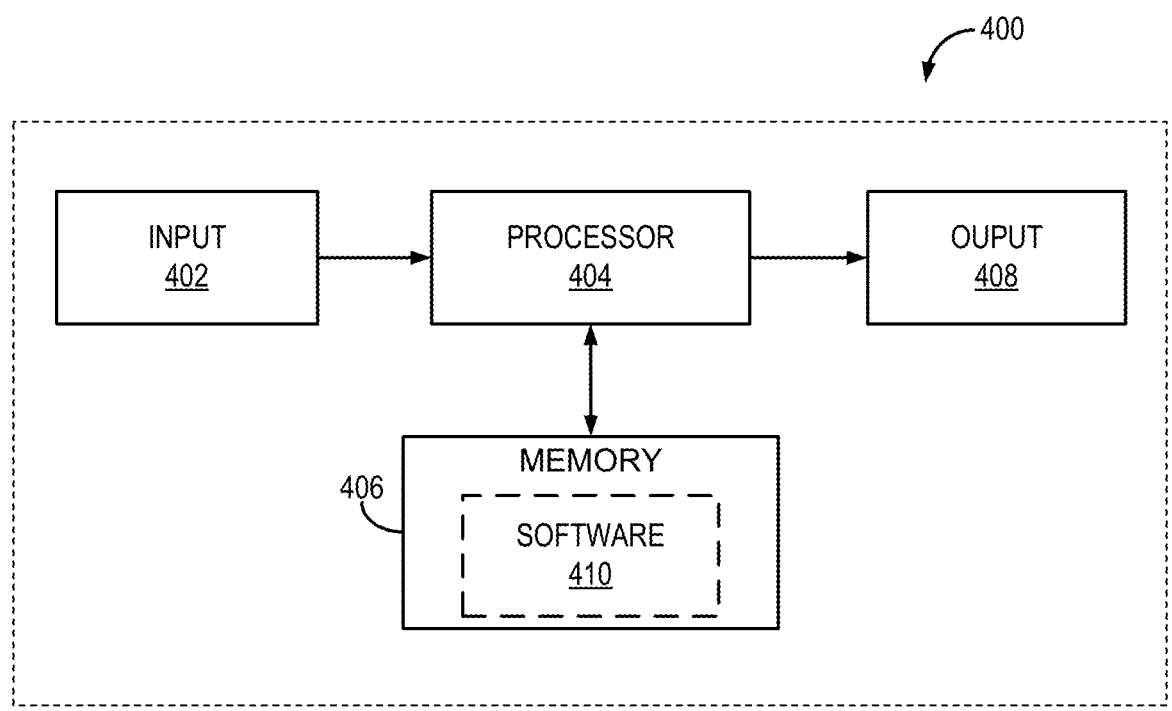
FIG. 4 is a block schematic diagram of a computer system configured in accordance with the present disclosure, for example, to carry out the steps of the method of FIG. 3.

Referring to FIG. 4, a block diagram of an example computer system 400 that can be used for performing the above-described model building and/or carry out the analysis described above with respect to FIG. 3 is illustrated. The system 400 may include an input 402, at least one processor 404, a memory 406, and an output 408. The system 400 may be, for example, a workstation, a notebook computer, a portable tablet, a personal digital assistant ("PDA"), a multimedia device, a smartphone, a network server, a mainframe, or any other general-purpose or application-specific computing device. The computer system 400 may operate autonomously or semi-autonomously, or may read executable software instructions from a computer-readable medium (such as a hard drive, a CD-ROM, flash memory, and the like), or may receive instructions from a user, or any another source logically connected to a computer or device, such as another networked computer or server, via the input 402.

The input 402 may take a variety of shapes or forms, as desired, for operation of the computer system 400, including the ability for selecting, entering, or otherwise specifying parameters consistent with operating the computer system 400. For example, the input 402 may include user interface elements and/or network connections to receive user selections of models or therapies, or to load previously-constructed models. Among the processing tasks for operating the computer system 400, the at least one processor 404 may be configured to perform the methods described above with respect to FIG. 3. To this end, the memory 406 may contain software 410, and may be configured for storage and retrieval of processed information and data to be processed by the processor 404.

Figure 5:
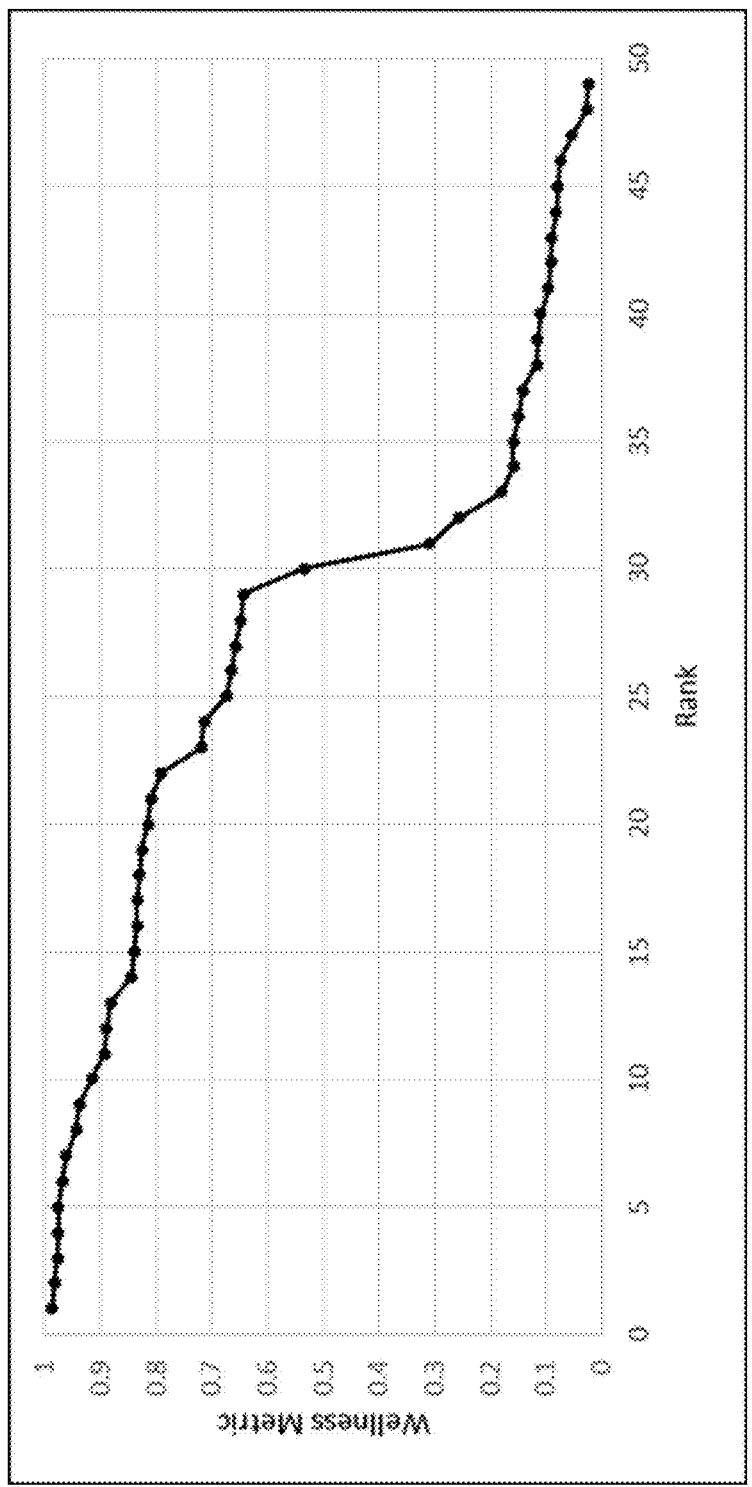
FIG. 5 is a graph showing wellness metric (WM) vs. rank for all agents with non-zero WM. WM for potentially efficacious virtual agents is depicted, in decreasing order of rank. The most effective virtual agent had a WM of 0.987, and the least effective one had a WM of 0.025.

The output 408 may be a network connection for communicating reports, such as described above with respect to process block 322 of FIG. 3, to other computers or users. Also, the output 408 may include a display for displaying text or graphical reports, such as will be described with respect to FIGS. 5 and 6. Furthermore, the output 408 may include a printer or other systems for communicating written or physical reports.

In one non-limiting example, the model described above was implemented using the GEneral NEural SImulation System (GENESIS) version 2.3, using programs written in C++ with message passing interface (MPI) to conduct parameter searches. The backward Euler integration method, as implemented in standard GENESIS, was used to solve equations, with a 0.1 msec time step. All modeling was carried out on a 72-processor dedicated Beowulf computer cluster (PSSC [Professional Service Super Computer] Labs, Lake Forest, Calif.) running under Red Hat Enterprise Linux 5 64-bit operating system within the Laboratory for Computational Neuroscience at McLean Hospital. One second of brain time required approximately one hour of CPU time.

2. Example

Figure 6:
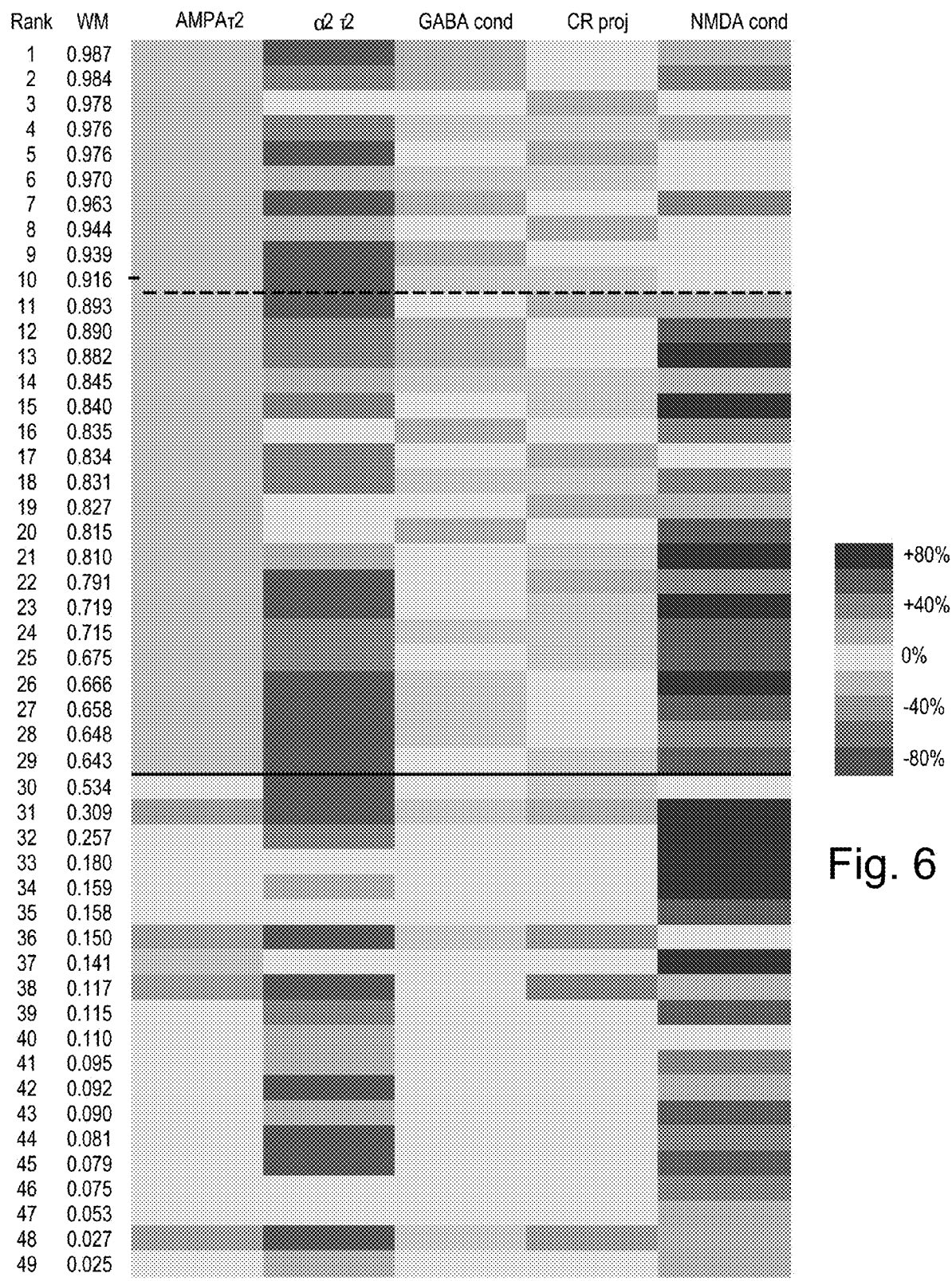
FIG. 6 is a graphical representation of 49 simulated agents with predicted efficacy. Each row represents a virtual drug, ordered from most (top) to least (bottom) effective, based on WM readout. In each column, coloration indicates the degree to which that cellular level effect is increased, or decreased, compared with baseline. Yellow indicates no change. Thus, WM=wellness metric; AMPA $\tau 2$=decay time constant of AMPA receptor; $\alpha 2\tau 2$ decay time constant of GABA $\alpha 2/\alpha 3$ receptor; GABA cond=generalized conductance of GABA synapses; CR proj=strength of CR projection; and NMDA cond=conductance of NMDA channel. The most effective virtual agent is associated with a modest decrease in AMPA$\tau 2$ time constant (to 2.5 ms), a significant decrease in $\alpha 2\tau 2$ (of 75%), a slight increase in generalized GABA inductance (of 20%), no change in CR projection strength, and a modest increase in NMDA conductance (of 20%). Solid line indicates demarcation between agents with WM>0.6 and those<0.6, corresponding to discontinuity in FIG. 5. Dashed line is drawn to (arbitrarily) indicate those agents with WM>0.9.

Applying the methodology described above, a study was conducted. In the study 49 virtual agents were identified with a non-zero wellness metric, representing 49 potentially efficacious drugs. The WM of each of these virtual agents, from highest to lowest, is displayed in graphical form in FIG. 5. It can be seen that there is a discontinuity in this curve at about WM=0.6, with a group of 29 virtual agents above this level. To get a sense, at a granular level, of what combination of cellular level effects were associated with the more effective virtual agents, all 49 simulated drugs are represented in "heat map" form in FIG. 6. The heat map of FIG. 6 is one non-limiting example of a report that may be generated at process block 322 of FIG. 3. Other non-limiting examples include text-based reports, other visualizations, and the like.

While FIG. 6 shows that particular effects may be associated with better outcomes, it illustrates that interactions between effects also play a significant role. To understand these, we ran a three-way ANOVA on the 49 top virtual medications; results are shown in Table 3. Analysis of variance was carried out on top 49 agents using wellness metric as the outcome measure, and taking cellular level manipulation as factors. Highly statistically significant effects (p<0.001) are indicated (*). See FIG. 3 caption for abbreviations.

TABLE 3

| Simulated Drug Effect | F value | p value |
|---|---|---|
| $\alpha_2 \tau_2$ | 25.88 | 3.33E–05* |
| GABA cond | 291.55 | 6.26E–15* |
| AMPA $\tau_2$ | 79.61 | 4.33E–09* |
| CR proj | 1.90 | 0.18 |
| NMDA cond | 33.05 | 6.33E–06* |
| $\alpha_2 \tau_2$: GABA cond | 16.08 | .00051* |
| $\alpha_2 \tau_2$: AMPA $\tau_2$ | 233.36 | 7.29E–14* |
| GABA cond: AMPA $\tau_2$ | 234.99 | 6.76E–14* |
| $\alpha_2 \tau_2$: CR proj | 57.63 | 7.88E–8* |
| GABA cond: CR proj | 0.77 | 0.388 |
| AMPA $\tau_2$: CR proj | 229.71 | 8.66E–14* |
| $\alpha_2 \tau_2$: NMDA cond | 2.89 | 0.102 |
| GABA cond: NMDA cond | 6.56 | 0.017 |
| AMPA $\tau_2$: NMDA cond | 0.58 | 0.455 |
| CR proj: NMDA cond | 0.01 | 0.909 |
| $\alpha_2 \tau_2$: GABA cond: CR proj | 0.25 | 0.619 |
| GABA cond: $\alpha_2 \tau_2$: CR proj | 0.72 | 0.404 |
| $\alpha_2 \tau_2$: GABA cond: NMDA cond | 0.64 | 0.431 |
| $\alpha_2 \tau_2$: AMPA $\tau_2$: NMDA cond | 3.53 | 0.073 |
| GABA cond: AMPA $\tau_2$: NMDA cond | 0.03 | 0.858 |
| $\alpha_2 \tau_2$: CR proj: NMDA cond | 0.05 | 0.831 |
| GABA cond: CR proj: NMDA cond | 5.89 | 0.023 |
| AMPA $\tau_2$: CR proj: NMDA cond | 3.51 | 0.073 |
| $\alpha_2 \tau_2$: GABA cond: CR proj: NMDA cond | 1.04 | 0.318 |

Of note, at the single effect level, two of the novel mechanisms investigated ($\alpha_2\tau_2$ and AMPA$\tau_2$) showed highly significant ameliorative effects. Perhaps more interestingly, there was marked synergism between effects: a simulated medication with combined decrease in $\alpha_2\tau_2$ and decrease in AMPA$\tau_2$ showed a robust and highly significant anti-schizophrenic effect. However, increasing NMDA (which, as an individual intervention, showed a highly significant positive effect) in conjunction with decreasing $\alpha_2\tau_2$ showed a weak and non-significant effect. Also, AMPA$\tau_2$, which as a single intervention showed a positive but modest effect (F=79.61), showed large highly significant effectiveness when combined with CR and GABA effects, with F=229.71 and F=234.99, respectively.

Thus, as can be seen from, for example, FIG. 6, a method can be provided for evaluating an effectiveness of a drug for treating a psychological condition. The method can include generating a report of effectiveness of a virtual drug compared to a testing construct, such as the model described above or even a pathological tissue sample. The report can include an indication of positive efficacy upon determining one of the following: causing a decrease in a decay time constant of an alpha2 receptor (alpha2tau2); causing a decrease in a decay time constant of an alpha2 receptor (alpha2tau2) in combination with increasing generalized γ-aminobutyric acid (GABA) conductance; causing a decrease in a decay time constant of an alpha2 receptor (alpha2tau2) in combination with decreasing AMPA synapse decay time constant (AMPAtau2); causing a decrease in a decay time constant of an alpha2 receptor (alpha2tau2) in combination with increasing CR cell projection strength; causing a decrease in AMPA synapse decay time constant (AMPAtau2); causing a decrease in AMPA synapse decay time constant (AMPAtau2) in combination with increasing CR cell projection strength; causing increasing generalized γ-aminobutyric acid (GABA) conductance in combination with decreasing AMPA synapse decay time constant (AMPAtau2); causing increasing generalized γ-aminobutyric acid (GABA) conductance in combination with increasing N-methyl-D-asparate (NMDA) conductance; causing increasing generalized γ-aminobutyric acid (GABA) conductance in combination with increasing CR cell projection strength and increasing N-methyl-D-asparate (NMDA) conductance; or other indicators.

3. Discussion

Among medical conditions, developing drugs for psychiatric conditions is uniquely difficult given the extraordinary complexity of the human brain, an organ with an estimated 86 billion neurons and $10^{14}$-$10^{15}$ synapses. Normal cognitive processes, as well as the symptoms of psychiatric illness, are emergent properties of the system (Beggs 2008), and as such it is difficult or impossible to predict, a priori, the system level effects of a particular neuron level intervention or set of interventions—it is a problem that calls out for a systems biology approach (Montague et al. 2012).

In just the above-described example study, the computational methodology detailed here identified a number of non-obvious, potentially efficacious virtual drugs for the treatment of schizophrenia. Notably, the virtual agents identified were not simple reversals of the causative lesions. Also, the example study identified unique combinations of effects for potential anti-schizophrenic agents. The efficacy of the simulated agents identified could not have been predicted in advance, and this exhibits the unique contribution such computational methodologies could make to the discovery of fundamentally new psychiatric medications.

3.1 Generalizability

While the example presented herein describe one, non-limiting example of a biomarker (ASSR deficit) for one, non-limiting example of one particular illness (schizophrenia), for one, non-limiting example of one brain area (hippocampus), the systems and methods described herein are not limited to these examples. For example, in addition to the gamma-band oscillatory abnormalities described above, schizophrenic patients have well-documented deficits in working memory tasks—that is, the ability to hold percepts or cognitions "on line" for brief (10 seconds or less) periods of time (J. Lee and Park 2005; Piskulic et al. 2007)—and this is felt to be subserved by prefrontal cortex. Models quantitatively replicating human performance on this task in the control (Brunel and Wang 2001; Barak and Tsodyks 2014; Durstewitz et al. 2000) and schizophrenic conditions (Cano-Colino and Compte 2012) have been described. The above-described systems and methods can be readily expanded to use one or more, including a battery, of model systems focused on different biomarkers, in light of the multiple brain areas affected in schizophrenia or other illnesses.

As another example, patients with Alzheimer's disease show particular deficits in the paired associate learning task, which is felt to be hippocampally mediated; these deficiencies are not seen to the same quantitative extent in normal aging (Egerhazi et al. 2007; O'Connell et al. 2004), or those with other psychiatric illnesses (Swainson et al. 2001; A. C. Lee et al. 2003; Granholm and Butters 1988). This task also has been computationally modeled in the control (Rizzuto and Kahana 2001; Hasselmo and Wyble 1997) and diseased (Zhao et al. 2010) states. Another example is fragile X syndrome (FXS), which is the most commonly occurring cause of mental retardation in boys, affecting one out of 4,000 males and one out of 8,000 females. FXS patients show particular difficulty in tasks requiring sequential memory (such as the digit span test), as opposed to those requiring simultaneous processing (such as Gestalt perception) (Baker et al. 2011; Dykens et al. 1987; Freund and Reiss 1991; Hodapp et al. 1992; Van der Moen et al. 2010). Sequencing tasks have been modeled in the control (O'Reilly and Soto 2006) and in the fragile X-positive (Johnson-Glenberg 2008) states. The above-described systems and methods can also be used in these contexts.

The above described systems and methods define a parameter space of potentially beneficial neural level effects. As the example detailed here has demonstrated, the inspiration for these initial hypotheses can derive from a number of sources. First, medications which have shown some efficacy, and whose pharmacologic effects are known, can be included. Second, recent basic neuroscience research on psychiatric conditions has suggested numerous potential genetic and other brain-based etiologies in ways that, even twenty years ago would have been unimaginable. For example, autism was once felt to arise from deficiencies in parenting. It is now known that there is a significant genetic contribution to this disorder, and it is one of the most heritable of all psychiatric illnesses (Smoller et al. 2008). Recent reviews (Persico and Napolioni 2013) have enumerated large numbers of possible neuroanatomic dysfunctions in the illness (Amaral et al. 2008).

Furthermore, computational models have the advantage of being transparent. Thus, the mechanisms by which particular biomarker abnormalities can be exacerbated or improved can be readily examined in an exploratory, trial-and-error manner, and findings can serve as the basis for additional "guesses." Also, while we have chosen to focus on synaptic and ion channel level effects, simulations can also include intracellular (e.g., second messenger mediated) interventions, as considerable work has been done on the detailed inclusion of such effects in cellular level computational models (Bhalla 2014).

Traditional drug discovery methodologies have often focused on a particular behavioral target, and evaluated this in animal models of the disease. However, doing such tests for each hypothesized ameliorative mechanism, one at a time, can be an exceedingly resource-intensive undertaking; to evaluate all combinations in animal models would be, practically speaking, infeasible. In the example described herein, we evaluated 2,000 virtual drugs on a 72-process supercomputer within a workable time period.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Thus, while the invention has been described above in connection with particular embodiments and examples, the invention is not necessarily so limited, and that numerous other embodiments, examples, uses, modifications and departures from the embodiments, examples and uses are intended to be encompassed by the claims attached hereto.

The entire disclosure of each patent and publication cited herein is incorporated by reference, as if each such patent or publication were individually incorporated by reference herein.

REFERENCES

The following references and any additional disclosed herein are each incorporated by reference in its entirety.

Amaral, D. G., Schumann, C. M., & Nordahl, C. W. (2008). Neuroanatomy of autism. *Trends Neurosci*, 31(3), 137-145, doi:10.1016/j.tins.2007.12.005.

American Psychiatric Association (2013). *Diagnostic and statistical manual of mental disorders: DSM-5* (5th ed.). Washington, D.C.: American Psychiatric Publishing.

Baker, S., Hooper, S., Skinner, M., Hatton, D., Schaaf, J., Ornstein, P., et al. (2011). Working memory subsystems and task complexity in young boys with Fragile X syndrome. *Journal of Intellectual Disability Research*, 55, 19-29.

Barak, O., & Tsodyks, M. (2014). Working models of working memory. *Curr Opin Neurobiol*, 25, 20-24, doi: 10.1016/j.conb.2013.10.008.

Beggs, J. M. (2008). The criticality hypothesis: how local cortical networks might optimize information processing. *Philos Trans A Math Phys Eng Sci*, 366(1864), 329-343, doi:10.1098/rsta.2007.2092.

Benes, F. M., & Berretta, S. (2001). GABAergic interneurons: implications for understanding schizophrenia and bipolar disorder. *Neuropsychopharmacology*, 25(1), 1-27.

Benes, F. M., Khan, Y., Vincent, S. L., & Wickramasinghe, R. (1996). Differences in the subregional and cellular distribution of $GABA_A$ receptor binding in the hippocampal formation of schizophrenic brain. *Synapse*, 22(4), 338-349.

Bhalla, U. S. (2014). Molecular computation in neurons: a modeling perspective. *Curr Opin Neurobiol*, 25, 31-37, doi:10.1016/j.conb.2013.11.006.

Biomarkers Definitions Working Group (2001). Biomarkers and surrogate endpoints: Preferred definitions and conceptual framework. *Clincial Pharmacology and Therapeutics*, 69(3), 89-95.

Bower, J. M., & Beeman, D. (1998). *The Book of GENESIS: Exploring Realistic Neural Models with the GEneral NEural Simulation System*. Santa Clara, Calif.: Springer-VerlagTelos.

Brunel, N., & Wang, X. J. (2001). Effects of neuromodulation in a cortical network model of object working memory dominated by recurrent inhibition. *J Comput Neurosci*, 11(1), 63-85.

Cano-Colino, M., & Compte, A. (2012). A computational model for spatial working memory deficits in schizophrenia. *Pharmacopsychiatry*, 45 Suppl 1, S49-56, doi: 10.1055/s-0032-1306314.

Casey, B. J., Oliveri, M. E., & Insel, T. (2014). A neurodevelopmental perspective on the research domain criteria (RDoC) framework. *Biol Psychiatry*, 76(5), 350-353, doi: 10.1016/j.biopsych.2014.01.006.

Cho, R. Y., Konecky, R. O., & Carter, C. S. (2006). Impairments in frontal cortical gamma synchrony and cognitive control in schizophrenia. *Proceedings of the National Academy of Sciences of the United States of America*, 103(52), 19878-19883.

Coyle, J. (2006). Glutamate and schizophrenia: beyond the dopamine hypothesis. *Cellular and Molecular Neurobiology*, 4-6, 365-384.

Coyle, J. T., Balu, D., Benneyworth, M., Basu, A., & Roseman, A. (2010). Beyond the dopamine receptor: novel therapeutic targets for treating schizophrenia. *Dialogues Clin Neurosci,* 12(3), 359-382.

De Schutter, E. (2013). Collaborative modeling in neuroscience: time to go open model? *Neuroinformatics,* 11(2), 135-136, doi:10.1007/s12021-013-9181-6.

Defelipe, J. (2011). The evolution of the brain, the human nature of cortical circuits, and intellectual creativity. *Front Neuroanat,* 5, 29, doi:10.3389/fnana.2011.00029.

Durstewitz, D., Seamans, J. K., & Sejnowski, T. J. (2000). Dopamine-mediated stabilization of delay-period activity in a network model of prefrontal cortex. *Journal of Neurophysiology,* 83, 1733-1750.

Dykens, E., Hodapp, R., & Leckman, J. (1987). Strengths and weaknesses in the intellectual functioning of males with fragile X syndrome. *American Journal of Mental Deficiency,* 92(2), 234-236.

Egerhazi, A., Berecz, R., Bartok, E., & Degrell, I. (2007). Automated neuropsychological test battery (CANTAB) in mild cognitive impairment and in Alzheimer's Disease. *Progress in Neuro-Psychopharmacology and Biological Psychiatry,* 31, 746-751.

Fatemi, S., Earle, J., & McMenomy, T. (2000). Reduction in reelin immunoreactivity in hippocampus of subjects with schizophrenia, bipolar disorder and major depression. *Molecular Psychiatry,* 5, 654-663.

Feinberg, I. (1982). Schizophrenia: caused by a fault in programmed synaptic elimination during adolescence? *Journal of Psychiatric Research,* 17, 319-334.

Freund, L. S., & Reiss, A. L. (1991). Cognitive profiles associated with the fra(X) syndrome in males and females. *American Journal of Medical Genetics,* 38, 542-547.

Fries, P., Reynolds, J. H., Rorie, A. E., & Desimone, R. (2001). Modulation of oscillatory neuronal synchronization by selective visual attention. *Science,* 291(5508), 1560-1563, doi:10.1126/science.291.5508.1560.

Gandal, M. J., Edgar, J. C., Klook, K., & Siegel, S. J. (2012). Gamma synchrony: towards a translational biomarker for the treatment-resistant symptoms of schizophrenia. *Neuropharmacology,* 62(3), 1504-1518, doi:10.1016/j.neuropharm.2011.02.007.

Garey, L. J., Ong, W. Y., Patel, T. S., Kanani, M., Davis, A., Mortimer, A. M., et al. (1998). Reduced dendritic spine density on cerebral cortical pyramidal neurons in schizophrenia. *Journal of Neurology, Neurosurgery, and Psychiatry,* 65, 446-453.

Geerts, H., Spiros, A., Roberts, P., Twyman, R., Alphs, L., & Grace, A. A. (2012). Blinded prospective evaluation of computer-based mechanistic schizophrenia disease model for predicting drug response. *PLoS One,* 7(12), e49732, doi:10.1371/journal.pone.0049732.

Granholm, E., & Butters, N. (1988). Associative encoding and retrieval in Alzheimer's and Huntington's Disease. *Brain and Cognition,* 7, 335-347.

Gray, C. M., Konig, P., Engel, A. K., & Singer, W. (1989). Oscillatory responses in cat visual cortex exhibit intercolumnar synchronization which reflects global stimulus properties. *Nature,* 338(6213), 334-337, doi:10.1038/338334a0.

Hamm, J. P., Gilmore, C. S., Picchetti, N. A., Sponheim, S. R., & Clementz, B. A. (2011). Abnormalities of neuronal oscillations and temporal integration to low- and high-frequency auditory stimulation in schizophrenia. *Biological Psychiatry,* 69(10), 989-996, doi:10.1016/j.biopsych.2010.11.021.

Hasselmo, M. E., & Wyble, B. P. (1997). Free recall and recognition in a network model of the hippocampus: simulating effects of scopolamine on human memory function. *Behavioural Brain Research,* 89, 1-34.

Heckers, S., Stone, D., Walsh, J., Shick, J., Koul, P., & Benes, F. M. (2002). Differential Hippocampal Expression of Glutamic Acid Decarboxylase 65 and 67 Messenger RNA in Bipolar Disorder and Schizophrenia. *Archives of General Psychiatry,* 59(6), 521-529.

Hodapp, R., Leckman, J., Dykens, E., Sparrow, S., Zelinsky, D., & Ort, S. (1992). K-ABC profiles in children with fragile X syndrome, Down syndrome, and nonspecific mental retardation. *American Journal of Mental Retardation,* 97(1), 39-46.

Hoffman, R. E., & McGlashan, T. H. (2003). Schizophrenia: From psychodynamic to neurodynamic theories. In J. S. Sadock, & V. A. Sadock (Eds.), *Kaplan and Sadock's Synopsis of Psychiatry* (9th ed., Vol. 1). Philadelphia, Pa.: Lippincott Williams and Wilkins.

Howes, O. D., Kambeitz, J., Kim, E., Stahl, D., Slifstein, M., Abi-Dargham, A., et al. (2012). The nature of dopamine dysfunction in schizophrenia and what this means for treatment. *Arch Gen Psychiatry,* 69(8), 776-786, doi: 10.1001/archgenpsychiatry.2012.169.

Hughes, J. R. (2008). Gamma, fast, and ultrafast waves of the brain: their relationships with epilepsy and behavior. *Epilepsy Behav,* 13(1), 25-31, doi:10.1016/j.yebeh.2008.01.011.

Jadi, M. P., Margarita Behrens, M., & Sejnowski, T. J. (2015). Abnormal Gamma Oscillations in N-Methyl-D-Aspartate Receptor Hypofunction Models of Schizophrenia. *Biol Psychiatry,* doi:10.1016/j.biopsych.2015.07.005.

Javitt, D., Spencer, K., Thaker, G., Winterer, G., & Hajos, M. (2008). Neurophysiological biomarkers for drug development in schizophrenia. *Nature Reviews Drug Discovery,* 7, 68-83.

Johnson-Glenberg, M. (2008). Fragile X syndrome: Neural network models of sequencing and memory. *Cognitive Systems Research,* 9, 274-292.

Kessler, R. C., Berglund, P., Demler, O., Jin, R., Merikangas, K. R., & Walters, E. E. (2005). Lifetime prevalence and age-of-onset distributions of DSM-IV disorders in the National Comorbidity Survey Replication. *Arch Gen Psychiatry,* 62(6), 593-602, doi:10.1001/archpsyc.62.6.593.

Kirli, K. K., Ermentrout, G. B., & Cho, R. Y. (2014). Computational study of NMDA conductance and cortical oscillations in schizophrenia. *Front Comput Neurosci,* 8, 133, doi:10.3389/fncom.2014.00133.

Krishnan, G. P., Hetrick, W. P., Brenner, C. A., Shekhar, A., Steffen, A. N., & O'Donnell, B. F. (2009). Steady state and induced auditory gamma deficits in schizophrenia. *Neuroimage,* 47(4), 1711-1719.

Kwon, J. S., O'Donnell, B. F., Wallenstein, G. V., Greene, R. W., Hirayasu, Y., Nestor, P. G., et al. (1999). Gamma frequency-range abnormalities to auditory stimulation in schizophrenia. *Arch Gen Psychiatry,* 56(11), 1001-1005.

Labbate, L. A., Fava, M., Rosenbaum, J. F., & Arana, G. W. (2010). *Handbook of Psychiatric Drug Therapy* (6th ed.). Philadelphia: Lippincott Williams and Wilkins.

Law, A., Weickert, C., Hyde, T., Kleinman, J., & Harrison, P. (2004). Reduced spinophilin but not microtubule-associated protein 2 express in the hippocampal formation in schizohprenia and mood disorders: Molecular evidence for a pathology of dendritic spines. *American Journal of Psychiatry,* 161, 1848-1855.

Lee, A. C., Rahman, S., Hodges, J., Sahakian, B., & Graham, K. (2003). Associative and recognition memory for novel objects in dementia: implications for diagnosis. *European Journal of Neuroscience,* 18, 1660-1170.

Lee, J., & Park, S. (2005). Working memory impairments in schizohprenia: A meta analysis. *Journal of Abnormal Psychology,* 114(4), 599-611.

Light, G. A., Hsu, J. L., Hsieh, M. H., Meyer-Gomes, K., Sprock, J., Swerdlow, N. R., et al. (2006). Gamma band oscillations reveal neural network cortical coherence dysfunction in schizophrenia patients. *Biol Psychiatry,* 60(11), 1231-1240, doi:10.1016/j.biopsych.2006. 03.055.

Lisman, J., Coyle, J., Green, R., Javitt, D., Benes, F., Heckers, S., et al. (2008). Circuit-based framework for understanding neurotransmitter and risk gene interactions in schizophrenia. *Trends in Neuroscience,* 31(5), 234-242.

Meyer-Lindenberg, A., & Weinberger, D. (2006). Intermediate phenotypes onad genetic mechanisms of psychatic disorders. *Nature Reviews Neuroscience,* 7, 818-827.

Miller, G. (2010). Psychiatry. Beyond DSM: seeking a brain-based classification of mental illness. *Science,* 327 (5972), 1437, doi:10.1126/science.327.5972.1437.

Montague, P. R., Dolan, R. J., Friston, K. J., & Dayan, P. (2012). Computational psychiatry. *Trends Cogn Sci,* 16(1), 72-80, doi:10.1016/j.tics.2011.11.018.

Moran, L. V., & Hong, L. E. (2011). High vs low frequency neural oscillations in schizophrenia. *Schizophrenia Bulletin,* 37(4), 659-663, doi:10.1093/schbul/sbr056.

Nestler, E., & Hyman, S. (2010). Animal models of neuropsychiatric disorders. *Nat Neurosci,* 13(10), 1161-1169.

Nunes, E. A., MacKenzie, E. M., Rossolatos, D., Perez-Parada, J., Baker, G. B., & Dursun, S. M. (2012). D-serine and schizophrenia: an update. *Expert Rev Neurother,* 12(7), 801-812, doi:10.1586/ern.12.65.

Nunez, P. L. (1981). *Electric fields of the brain: The neurophysics of EEG.* New York: Oxford University Press.

O'Connell, H., Coen, R., Kidd, N., Warsi, M., Chin, A.-V., & Lawlor, B. (2004). Early detection of Alzheimer's disease (AD) using the CANTAB paired associates learning test. *International Journal of Geriatric Psychiatry,* 19, 1207-1208.

O'Reilly, R. C., & Soto, R. (2006). A Model of the Phonological Loop: Generalization and Binding. In T. Dietterich, S. Becker, & Z. Ghahramani (Eds.), *Advances in Neural Information Processing Systems (NIPS)* 14. Cambridge, Mass.: MIT Press.

Ongur, D., & Price, J. L. (2000). The organization of networks within the orbital and medial prefrontal cortex of rats, monkeys and humans. *Cereb Cortex,* 10(3), 206-219.

Perlis, R. (2011). Translating biomarkers to clinical practice. *Molecular Psychiatry,* 16, 1076-1087.

Persico, A. M., & Napolioni, V. (2013). Autism genetics. *Behav Brain Res,* 251, 95-112, doi:10.1016/j.bbr.2013.06.012.

Piskulic, D., Olver, J. S., Norman, T. R., & Maruff, P. (2007). Behavioural studies of spatial working memory dysfunction in schizophrenia: A quantitative literature review. *Psychiatry Research,* 150,111-121.

Pittman-Polletta, B. R., Kocsis, B., Vijayan, S., Whittington, M. A., & Kopell, N. J. (2015). Brain rhythms connect impaired inhibition to altered cognition in schizophrenia. *Biol Psychiatry,* 77(12), 1020-1030, doi:10.1016/j.biopsych.2015.02.005.

Rizzuto, D., & Kahana, M. (2001). An autoassociative neural network model of paired-associate leaning. *Neural Computation,* 13, 2075-2092.

Shouval, H. Z., Bear, M. F., & Cooper, L. N. (2002). A unified model of NMDA receptor-dependent bidirectional synaptic plasticity. *Proc Natl Acad Sci USA,* 99(16), 10831-10836, doi:10.1073/pnas.152343099.

Siekmeier, P. J. (2009). Evidence of multistability in a realistic computer simulation of hippocampus subfield CA1. *Behavioural Brain Research,* 200, 220-231.

Siekmeier, P. J. (2015). Computational modeling of psychiatric illnesses via well-defined neurophysiological and neurocognitive biomarkers. *Neuroscience and Biobehavioral Reviews,* 57, 365-380, doi:10.1016/j.neubiorev.2015.09.014.

Siekmeier, P. J., & vanMaanen, D. P. (2013). Development of antipsychotic medications with novel mechanisms of action based on computational modeling of hippocampal neuropathology. *PLoS One,* 8(3), e58607, doi:10.1371/journal.pone.0058607.

Siekmeier, P. J., & vanMaanen, D. P. (2014). Dopaminergic contributions to hippocampal pathophysiology in schizophrenia: a computational study. *Neuropsychopharmacology,* 39(7), 1713-1721, doi:10.1038/npp.2014.19.

Singh, I., & Rose, N. (2009). Biomarkers in psychiatry. *Nature,* 460(7252), 202-207, doi:10.1038/460202a.

Smoller, J. W., Sheidley, B. R., & Tsuang, M. T. (2008). *Psychiatric Genetics: Applications to Clinical Practice.* Arlington, Va.: American Psychiatric Publishing.

Spencer, K. M., Salisbury, D. F., Shenton, M. E., & McCarley, R. W. (2008). Gamma-band auditory steady-state responses are imparied in first episode psychosis. *Biological Psychiatry,* 64, 369-375.

Swainson, R., Hodges, J., Galton, C., Semple, J., Michael, A., Dunn, B., et al. (2001). Early detection and differential diagnosis of Alzheimer's disease and depression with neuropsychological tasks. *Dementia and Geriatric Cognitive Disorders,* 12(4), 265-280.

Tallon-Baudry, C., & Bertrand, O. (1999). Oscillatory gamma activity in humans and its role in object representation. *Trends Cogn Sci,* 3(4), 151-162.

Teale, P., Collins, D., Maharajh, K., Rojas, D., Kronberg, E., & Reite, M. (2008). Cortical Source estimates of gamma band amplitude and phase are different in schizophrenia. *Neuroimage,* 42, 148101489.

Torrey, E., Barci, B., Webster, M., Bartko, J., Meador-Woodruff, J., & Knable, M. (2005). Neurochemical markers for schizophrenia, bipolar disorder, and major depression in postmortem brains. *Biological Psychitry,* 57, 252-260.

Traub, R. D., Jefferys, J. G., Miles, R., Whittington, M. A., & Toth, K. (1994). A branching dendritic model of a rodent CA3 pyramidal neurone. *Journal of Physiology (London),* 481, 79-95.

Traub, R. D., & Miles, R. (1995). Pyramidal cell-to-inhibitory cell spike transduction explicable by active dendritic conductances in inhibitory cell. *Journal of Computational Neuroscience,* 2(4), 291-298.

Tsuchimoto, R., Kanba, S., Hirano, S., Oribe, N., Ueno, T., Hirano, Y., et al. (2011). Reduced high and low frequency gamma synchronization in patients with chronic schizophrenia. *Schizophrenia Research,* 133(1-3), 99-105, doi: 10.1016/j.schres.2011.07.020.

Uhlhaas, P. J., Linden, D. E., Singer, W., Haenschel, C., Lindner, M., Maurer, K., et al. (2006). Dysfunctional long-range coordination of neural activity during Gestalt perception in schizophrenia. *J Neurosci,* 26(31), 8168-8175, doi:10.1523/JNEURO SCI.2002-06.2006.

Uhlhaas, P. J., & Singer, W. (2010). Abnormal neural oscillations and synchrony in schizophrenia. *Nat Rev Neurosci,* 11(2), 100-113.

Uhlhaas, P. J., & Singer, W. (2015). Oscillations and neuronal dynamics in schizophrenia: the search for basic symptoms and translational opportunities. *Biological Psychiatry,* 77(12), 1001-1009, doi:10.1016/j.biopsych.2014.11.019.
Van der Moen, M., Huizinga, M., Huizenga, H., Ridderinkhof, K., Van der Molen, M., Hamel, B., et al. (2010). Profiling fragile X syndrome in males: Strengths and weaknesses in cognitive abilities. *Research in Developmental Disabilities,* 31, 426-439.
Vierling-Claassen, D., Siekmeier, P., Stufflebeam, S., & Kopell, N. (2008). Modeling GABA alterations in schizophrenia: a link between impaired inhibition and altered gamma and beta range auditory entrainment. *Journal of Neurophysiology,* 99(5), 2656-2671.
Wilson, T., Hernandez, O., Asherin, R., Teale, P., Reite, M., & Rojas, D. (2008). Cortical gamma generators suggest abnormal auditory circuitry in early-onset psychosis. *Cereb Cortex,* 18, 371-378.
Woo, W., Whitehead, R. E., Melchitzky, D. S., & Lewis, D. A. (1998). A subclass of prefrontal gamma-aminobutyric acid axon terminals are selectively altered in schizophrenia. *Proceedings of the National Academy of Sciences of the U.S.A.,* 95, 5341-5346.
World Health Organization (2001). The world health report 2001 mental health: new understanding, new hope. (pp. xviii, 178 p.). Geneva: World Health Organization.
Zhao, W., Qiao, Q., & Wang, D. (2010). A Hopfield-like hippocampal neural network model for studying associative memory in Alzheimer's disease. *Neural Regeneration Research,* 5(22), 1694-1700.

I claim:

1. A computer system comprising:
   a non-transitory memory having stored thereon a computational model for a psychological condition and a computational control model and having instructions for evaluating an effectiveness of a therapy for a psychological condition;
   a processor configured to access the memory and carry out steps comprising:
   (i) selecting a therapy to be analyzed for effectiveness for the psychological condition, the therapy represented by a virtual therapy;
   (ii) applying the virtual therapy selected in step (i) to the computational model of the psychological condition by introducing at least one simulated therapy effect to the model to simulate at least one physiological parameter, wherein the model includes hyperdopaminergia as a function;
   (iii) determining a response using the at least one simulated physiological parameter;
   (iv) comparing the response to the computational control model to determine a wellness metric; and
   (v) generating a report indicating an effectiveness of the therapy based on the wellness metric;
   wherein the wellness metric is calculated as:

$$WM = 1 - \left(\frac{1}{D_X} \times |\Delta P_X|\right);$$

wherein WM is the wellness metric, Dx represents a deficit in response associated with the psychological condition at a selected biomarker condition, X, at baseline, compared with the control model, and $\Delta P_X$ is given by:

$$\Delta P_X = \frac{P_{X,s} - P_{X,c}}{P_{X,c}};$$

and
wherein $P_{X,s}$ is the response from the computational model of the psychological condition at the selected biomarker condition, X, and $P_{X,c}$ is the response from the computational control model at the selected biomarker condition, X.

2. The computer system of claim 1 wherein the therapy is a drug and wherein the processor is further configured to apply a virtual drug representing the drug to the computational model of the psychological condition by introducing at least one simulated medication effect to the model to carry out step (ii).

3. The computer system of claim 1 wherein the computational model of the psychological condition is configured to cause the processor to model increases in dopamine levels as a decrement in gamma band response.

4. The computer system of claim 1 wherein the computational control model is configured to cause the processor to model increases in dopamine levels as an enhancement of gamma band activity.

5. The computer system of claim 1 wherein the processor is further configured to:
   use auditory steady state response (ASSR) tasks as a biomarker for the psychological condition;
   compare the ASSR tasks when the virtual therapy is applied to the computational model of the psychological condition to ASSR tasks of the computational control model; and
   indicate a positive effectiveness of the therapy if the ASSR tasks when the therapy is applied to the model of the psychological condition approach ASSR tasks of the control model.

6. The computer system of claim 5 wherein the response includes a power response and is determined for ASSR tasks at 20 Hz ($P_{20,s}$), 30 Hz ($P_{30,s}$), and 40 Hz ($P_{40,s}$).

7. The computer system of claim 1 wherein the wellness metric is calculated by evaluating an indiscriminate effect and a detrimental effect of the virtual therapy indicated by the computational model of the psychological condition.

8. The computer system of claim 1 wherein the wellness metric is based on a difference in a power response given by the computational model of the psychological condition and a baseline power response.

9. The computer system of claim 1 wherein the psychological condition includes schizophrenia and the therapy includes a virtual drug.

10. A method for evaluating an effectiveness of a therapy for a psychological condition, the method including steps comprising:
   (i) selecting a therapy to be analyzed for effectiveness for the psychological condition, the therapy represented by a virtual therapy;
   (ii) applying the virtual therapy selected in step (i) to a computational model of the psychological condition by introducing at least one simulated therapy effect to the model to simulate at least one physiological parameter, wherein the model includes hyperdopaminergia as a function;
   (iii) determining a response using the at least one simulated physiological parameter;
   (iv) comparing the response to a control to determine a wellness metric; and (v) generating a report indicating an effectiveness of the therapy based on the wellness metric;

wherein the wellness metric is calculated as:

$$WM = 1 - \left(\frac{1}{D_X} \times |\Delta P_X|\right);$$

wherein WM is the wellness metric, Dx represents a deficit in response associated with the psychological condition at a selected biomarker condition, X, at baseline, compared with the computational control model, and $\Delta P_X$ is given by:

$$\Delta P_X = \frac{P_{X,s} - P_{X,c}}{P_{X,c}};$$

and wherein $P_{X,s}$ is the response from the computational model of the physiological condition at the selected biomarker condition, X, and $P_{X,c}$ is the response from the computational control model at the selected biomarker condition, X.

11. The method of claim 10 wherein the therapy is a drug and wherein step (ii) includes applying a virtual drug representing the drug to the model by introducing at least one simulated medication effect to the model.

12. The method of claim 10 wherein the model is configured to model increases in dopamine levels as a decrement in gamma band response.

13. The method of claim 10 wherein the control includes a computational control model and wherein the control model is configured to model increase in dopamine levels as an enhancement of gamma band activity.

14. The method of claim 10 wherein:
the model uses auditory steady state response (ASSR) tasks as a biomarker;
step (iv) includes comparing the ASSR tasks when the virtual therapy is applied to the model to a computational control model of ASSR tasks; and
step (v) includes indicating a positive effectiveness of the therapy if the ASSR tasks when the virtual therapy is applied to the model approach the control model of ASSR tasks.

15. The method of claim 14 wherein the response includes a power response determined for ASSR tasks at 20 Hz ($P_{20,s}$), 30 Hz ($P_{30,s}$), and 40 Hz ($P_{40,s}$) and the power response is compared to the computational control model of ASSR tasks.

16. The method of claim 10 wherein the wellness metric is calculated by evaluating an indiscriminate effect and a detrimental effect of the virtual therapy indicated by the model.

17. The method of claim 10 wherein the wellness metric is based on a difference in a power response given by the computational model and a baseline power response.

18. The method of claim 10 wherein the psychological condition includes schizophrenia and the therapy includes a virtual drug.

19. The method of claim 10 wherein the computational model indicates a decay time constant (tau2) property of a cell expressing functional 2-amino-3-(3-hydroxy-5-methyl-isoxazol 4 yl)propionic acid (AMPA) channel conductance in response to the virtual therapy.

20. The method of claim 10 wherein the computational model indicates an effect caused by the virtual therapy on a calretinin-positive (CR+) cell on its post-synaptic target, including γ-aminobutyric acid (GABA) synapse.

21. The method of claim 10 wherein the report indicates the therapy as having a positive effectiveness when causing a decrease in a decay time constant of an $alpha_2$ receptor ($alpha_2 tau_2$).

22. The method of claim 10 wherein the report indicates the therapy as having a positive effectiveness when causing a decrease in a decay time constant of an $alpha_2$ receptor ($alpha_2 tau_2$) in combination with increasing generalized γ-aminobutyric acid (GABA) conductance.

23. The method of claim 10 wherein the report indicates the therapy as having a positive effectiveness when causing a decrease in a decay time constant of an $alpha_2$ receptor ($alpha_2 tau_2$) in combination with decreasing AMPA synapse decay time constant ($AMPA tau_2$).

24. The method of claim 10 wherein the report indicates the therapy as having a positive effectiveness when causing a decrease in a decay time constant of an $alpha_2$ receptor ($alpha_2 tau_2$) in combination with increasing CR cell projection strength.

25. The method of claim 10 wherein the report indicates the therapy as having a positive effectiveness when causing a decrease in AMPA synapse decay time constant ($AMPA tau_2$).

26. The method of claim 10 wherein the report indicates the therapy as having a positive effectiveness when causing a decrease in AMPA synapse decay time constant ($AMPA tau_2$) in combination with increasing CR cell projection strength.

27. The method of claim 10 wherein the report indicates the therapy as having a positive effectiveness when causing increasing generalized γ-aminobutyric acid (GABA) conductance in combination with decreasing AMPA synapse decay time constant ($AMPA tau_2$).

28. The method of claim 10 wherein the report indicates the therapy as having a positive effectiveness when causing increasing generalized γ-aminobutyric acid (GABA) conductance in combination with increasing N-methyl-D-aspartate (NMDA) conductance.

29. The method of claim 10 wherein the report indicates the therapy as having a positive effectiveness when causing increasing generalized γ-aminobutyric acid (GABA) conductance in combination with increasing CR cell projection strength and increasing N methyl-D-aspartate (NMDA) conductance.

30. A method for evaluating an effectiveness of a drug for treating a psychological condition, the method including steps comprising:
(i) selecting a drug to be analyzed for effectiveness for the psychological condition, the drug represented by a virtual drug;
(ii) applying the virtual drug selected in step (i) to a computational model of the psychological condition by introducing at least one medication effect to the model to simulate at least one physiological parameter; and
(iii) generating a report indicating a positive effectiveness of the drug upon determining the following from step (ii):
causing increasing generalized .gamma.-aminobutyric acid (GABA) conductance in combination with increasing CR cell projection strength and increasing N-methyl-D-aspartate (NMDA) conductance.

* * * * *